(12) United States Patent
Shibaev et al.

(10) Patent No.: US 10,652,504 B2
(45) Date of Patent: May 12, 2020

(54) SIMPLE VIDEO COMMUNICATION PLATFORM

(71) Applicants: Georgiy Shibaev, Nepean (CA); Arnold Elite, Ottawa (CA); Junjie Yin, Ottawa (CA); Chandler Newman-Reed, Ottawa (CA); Zheng Lu, Kanata (CA); Michael A. J. Bourassa, Kanata (CA); Pengyu Chen, Kanata (CA); Michel Paquet, Kanata (CA)

(72) Inventors: Georgiy Shibaev, Nepean (CA); Arnold Elite, Ottawa (CA); Junjie Yin, Ottawa (CA); Chandler Newman-Reed, Ottawa (CA); Zheng Lu, Kanata (CA); Michael A. J. Bourassa, Kanata (CA); Pengyu Chen, Kanata (CA); Michel Paquet, Kanata (CA)

(73) Assignee: Aetonix Systems, Ottawa (CA)

( * ) Notice: Subject to any disclaimer, the term of this patent is extended or adjusted under 35 U.S.C. 154(b) by 0 days.

(21) Appl. No.: 16/119,741

(22) Filed: Aug. 31, 2018

(65) Prior Publication Data

US 2018/0376107 A1    Dec. 27, 2018

Related U.S. Application Data

(63) Continuation-in-part of application No. 15/288,963, filed on Oct. 7, 2016, which is a continuation of
(Continued)

(51) Int. Cl.
*H04N 7/14* (2006.01)
*G16H 80/00* (2018.01)
(Continued)

(52) U.S. Cl.
CPC .......... *H04N 7/147* (2013.01); *G06F 3/0488* (2013.01); *G06F 3/04886* (2013.01);
(Continued)

(58) Field of Classification Search
CPC combination set(s) only.
See application file for complete search history.

(56) References Cited

U.S. PATENT DOCUMENTS

| 6,020,915 A | 2/2000 | Bruno |
| 7,554,932 B1 | 6/2009 | Shurmantine |

(Continued)

OTHER PUBLICATIONS

International Search Report, PCT/IB2015/052290, 4 pages, dated Jul. 27, 2015.

*Primary Examiner* — Phung-Hoang J Nguyen
(74) *Attorney, Agent, or Firm* — Stratford Managers Corporation

(57) ABSTRACT

A system offering simplified bi-directional video communication between a user and a device of a pre-configured one or more persons of interest includes a touch display with a pictorial representation of each of the one or more persons of interest and a pictorial representation of one or more health indicators. The touch display is configured to establish the bi-directional video communication with a selected one of said persons of interest in response to a single touch of the pictorial representation of the selected one of the persons of interest. In one implementation, the system includes one or more biometric telemetry devices for acquiring and transmitting biometric data associated with a specific health indicator to the touch display, which is then transmitted to a database, processed and accessed by one or more authorized persons. In another implementation, the system includes a workflow engine for healthcare management of the patient.

20 Claims, 31 Drawing Sheets

Related U.S. Application Data application No. 14/670,512, filed on Mar. 27, 2015, now Pat. No. 9,491,206.

(60) Provisional application No. 62/051,036, filed on Sep. 16, 2014, provisional application No. 62/037,731, filed on Aug. 15, 2014, provisional application No. 61/971,929, filed on Mar. 28, 2014.

(51) Int. Cl.

| | | |
|---|---|---|
| H04N 5/232 | (2006.01) | |
| G06F 3/0488 | (2013.01) | |
| G08B 21/04 | (2006.01) | |
| H04N 7/15 | (2006.01) | |
| G16H 40/67 | (2018.01) | |
| H04L 29/06 | (2006.01) | |
| G16H 40/20 | (2018.01) | |
| A61B 5/00 | (2006.01) | |
| G08B 5/22 | (2006.01) | |
| G08B 21/24 | (2006.01) | |

(52) U.S. Cl.
CPC ....... *G08B 21/043* (2013.01); *G08B 21/0423* (2013.01); *G16H 40/20* (2018.01); *G16H 40/67* (2018.01); *G16H 80/00* (2018.01); *H04L 65/1069* (2013.01); *H04N 5/23206* (2013.01); *H04N 7/141* (2013.01); *H04N 7/15* (2013.01); *A61B 5/0022* (2013.01); *A61B 5/747* (2013.01); *G08B 5/22* (2013.01); *G08B 21/24* (2013.01); *H04L 65/403* (2013.01)

(56) References Cited

U.S. PATENT DOCUMENTS

| | | | |
|---|---|---|---|
| 9,547,977 B2 | 1/2017 | Will | |
| 2003/0050538 A1* | 3/2003 | Naghavi | G06F 19/3418 600/300 |
| 2003/0199780 A1 | 10/2003 | Page | |
| 2006/0178908 A1* | 8/2006 | Rappaport | G06F 19/325 705/2 |
| 2006/0212315 A1* | 9/2006 | Wiggins | G06F 19/328 705/2 |
| 2007/0186002 A1 | 8/2007 | Campbell | |
| 2008/0033256 A1* | 2/2008 | Farhan | G06F 19/3418 600/300 |
| 2008/0068447 A1 | 3/2008 | Mattila | |
| 2008/0129816 A1 | 6/2008 | Mattila | |
| 2009/0177495 A1* | 7/2009 | Abousy | G16H 50/20 705/3 |
| 2010/0198755 A1* | 8/2010 | Soll | G06F 19/324 706/11 |
| 2012/0054691 A1 | 3/2012 | Nurmi | |
| 2012/0088466 A1* | 4/2012 | Conroy | G06F 19/3418 455/404.1 |
| 2012/0293340 A1 | 11/2012 | Chan | |
| 2013/0130213 A1* | 5/2013 | Burbank | A61B 5/1118 434/236 |
| 2013/0179191 A1 | 7/2013 | Bal | |
| 2013/0215214 A1 | 8/2013 | Dhopte | |
| 2014/0052464 A1 | 2/2014 | Ray | |
| 2014/0108043 A1* | 4/2014 | Ach | G06Q 10/10 705/3 |
| 2014/0164022 A1* | 6/2014 | Reed | G06F 19/3481 705/3 |
| 2014/0269625 A1 | 9/2014 | Surface | |
| 2014/0278474 A1* | 9/2014 | McClure | G06F 19/3418 705/2 |
| 2015/0039396 A1 | 2/2015 | Ellis | |
| 2015/0173670 A1 | 6/2015 | Simon | |
| 2015/0352354 A1 | 12/2015 | Doerr | |
| 2016/0022144 A1 | 1/2016 | Hansen | |
| 2016/0042438 A1 | 2/2016 | Robertson | |
| 2016/0198319 A1 | 7/2016 | Huang | |
| 2016/0266645 A1 | 9/2016 | Marozau | |
| 2017/0026587 A1 | 1/2017 | Moberly | |
| 2017/0086672 A1 | 3/2017 | Tran | |

\* cited by examiner

SIMPLE VIDEO COMMUNICATION PLATFORM

CROSS REFERENCE TO RELATED APPLICATION

This application is a continuation-in-part of U.S. patent application Ser. No. 15/288,963 filed Oct. 7, 2016, which is a continuation of U.S. patent application Ser. No. 14/670,512 filed Mar. 27, 2015, which claims the benefit of U.S. Provisional Application No. 62/051,036, filed Sep. 16, 2014, U.S. Provisional Application No. 62/037,731, filed Aug. 15, 2014 and U.S. Provisional Application No. 61/971,929, filed Mar. 28, 2014, each of which is hereby incorporated by reference herein in its entirety.

FIELD OF THE INVENTION

The present disclosure relates to video communication, and in particular to a simple station enabling video communication and telemetry information gathering.

BACKGROUND

Seniors and people with special needs often face problems related to depression and health issues due to stress and social isolation. Many of these peoples live alone in a special care residence or at home. Often the fact that they are remote from family members leads to health issues. Overtime people lose interest to social activities, are getting socially disconnected, and get into a mode of expectation of family members showing up to visit them. This situation of social isolation leads to depression. There is a need to improve their communication with one or more POI (e.g. family member, friend, health care provider, residence staff).

Many families have a member at home that required continuous professional health care support. Often the professionals are remote and need to visit family required time. There is a need for a virtual remote care support to reduce health care cost while providing a more responsive service to patient in remote home. There is a need for a simple video communication system that works seamlessly across different devices and operating systems.

Furthermore, a workflow automation engine (i.e. "workflow engine") is usually used in business automation. For example, a workflow engine can automate processes such as sending emails or setting up web forms to be filled out. Such workflow engines are geared to very specific use cases. There have been workflows built-into healthcare information management applications for a variety of diseases. However, each new workflow is hand-integrated, while clients can only access pre-existing workflows. There is a need for a workflow engine for healthcare information management that provides workflows that can be updated for specific organizations in real-time without the need to update any applications. Such a workflow engine should be flexible enough to support any protocol involving collecting data from people, reacting to the collected data, and notifying others about data.

BRIEF SUMMARY

In accordance with one embodiment, a system offering one-touch bi-directional video communication between a user of a device and a pre-configured one or more persons of interest, and providing health information of the user to one or more persons of interest authorized to access the health information, said system comprising: a touch display with a pictorial representation of each of the one or more persons of interest and a pictorial representation of one or more health indicators; one or more biometric telemetry devices, each biometric telemetry device used for acquiring and transmitting biometric data associated with a specific health indicator to the touch display; wherein: said touch display is configured to establish said bi-directional video communication with a selected one of said persons of interest in response to a single touch of the pictorial represented of said selected one of said persons of interest, each biometric device is in two-way communication with said touch display; said touch display transmits said biometric data to a database for processing; said processed biometric data is accessed by the one or more persons of interest authorized to access the health information of the user.

In accordance with another embodiment, a system for managing healthcare of a patient, the system comprising: a system software application; a cloud server; a database; a plurality of healthcare workflow definitions; a forms engine; a workflow runtime module; and a task scheduler, wherein: the system software application is in communication with the cloud server, the cloud server is in communication with the database that stores the plurality of healthcare workflow definitions; the application retrieves the plurality of workflow definitions via the cloud server, a healthcare professional selects a workflow from the plurality of workflow definitions and completes a form generated by the forms engine; data in the form is submitted to the workflow runtime via the cloud server; the workflow runtime loads logic from the workflow definition to execute a next step in the workflow by and issues a first command to the cloud server to either: a) send one or more action items to one or more actors in the workflow via the application; or b) communicate with the task scheduler to create one or more tasks to be processed at a later time; and wherein the workflow runtime communicates a second command to the server to update healthcare information of the patient in the database.

In accordance with another embodiment, a workflow engine for healthcare information management, the workflow engine comprising: a system software application in communication with a cloud server; a plurality of workflow definitions stored in a database; a forms engine for generating a form in relation to the workflow definitions; a workflow runtime for executing logic in the workflow definition; and a scheduler module to create tasks, wherein: the server conveys the plurality of workflow definitions to the application; a person of interest selects a workflow from the plurality of workflow definitions and completes the form which is conveyed to the workflow runtime via the server; data from the form is communicated to the workflow runtime via the server; and the workflow runtime issues a first command to the cloud server to either:

a) send one or more action items to one or more actors in the workflow via the application; or b) communicate with a task scheduler to create one or more tasks to be processed at a later time; and wherein the workflow runtime communicates a second command to the server to update healthcare information of the patient in the database.

The foregoing and additional aspects and embodiments of the present disclosure will be apparent to those of ordinary skill in the art in view of the detailed description of various embodiments and/or aspects, which is made with reference to the drawings, a brief description of which is provided next.

BRIEF DESCRIPTION OF THE DRAWINGS

The foregoing and other advantages of the disclosure will become apparent upon reading the following detailed description and upon reference to the drawings.

Figure 1:
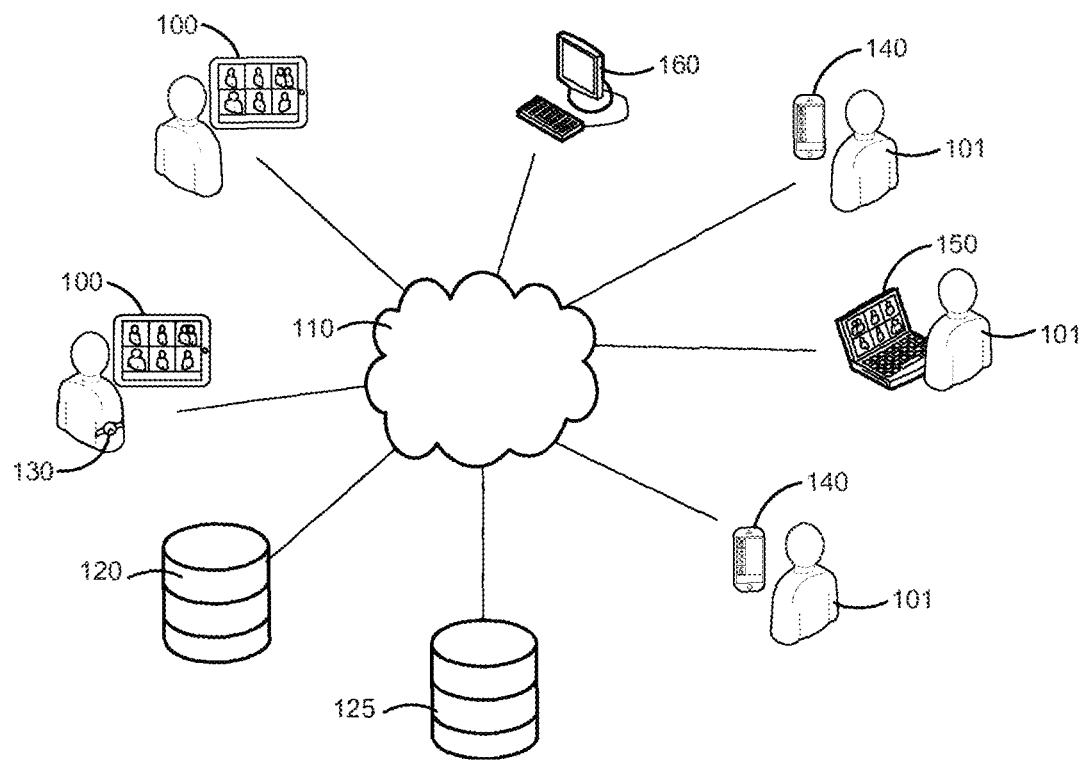
FIG. 1 is a high level diagram of the components of the system.

While the present disclosure is susceptible to various modifications and alternative forms, specific embodiments or implementations have been shown by way of example in the drawings and will be described in detail herein. It should be understood, however, that the disclosure is not intended to be limited to the particular forms disclosed. Rather, the disclosure is to cover all modifications, equivalents, and alternatives falling within the spirit and scope of an invention as defined by the appended claims.

DETAILED DESCRIPTION

A first embodiment, a Simple Video Station (SVS) is provided to seniors and people with special needs (referred to herein generically as "users"). The SVS has minimal user interaction capabilities other than allowing to establish video/voice communication with pre-determined POI (POI). Transparently, the SVS can optionally perform several other functions such as monitoring health information provided by biomedical telemetry systems or detecting emergency situation like fall or inactivity detection. The SVS also provide the user with medication reminders, emergency call, and other basic function.

The SVS is designed for users with limited mobility, minimal technical knowledge and possibly limited by cognitive impairment.

FIG. 1 gives an overview of the solution connectivity. One or more SVS 100 users can communicate with one or more predetermined POI 101. A software communication platform for biomedical telemetry and any other telemetry, which is managed by an integrated cloud computing solution for data analytics.

The SVS 100 allows a user to establish for video/audio connection with a single tap on a picture, corresponding to a POI 101. The POI 101 receives the call using an application on a smartphone or tablet 140 or on a computer 150. The SVS also has optional radio support for Zigbee®, Bluetooth® and WIFI® allowing connection to Internet over the air and to telemetry devices using Bluetooth® and Zigbee®. The SVS and applications are configured via a configuration database 125. The SVS connects to telemetry 130 devices surrounding the user which allow continuous transfer of data related to the user and/or the environment where the user lives via a telemetry database 120 to different applications. A central or distributed server 160 may also be used for configuration and monitoring of one or more SVS that are deployed. The configuration 125 and telemetry database 120 may be on the same file system. They may also be part of the server 160.

The data is transferred to a database 120 via a network 110, and is stored for analysis such as trending, data mining, and analytics. Notification, alarm, or recommendation can be provided to the POI based on the analysis. With that information, a POI can decide if an action is required or if everything is normal. Similar information is also available to family members which allow the families to be aware and assured of condition of relative. Assuming an abnormal situation, the system can notify a POI for immediate action and prevent undesired situation. If a doctor needs to be consulted, the SVS allow video/audio connection to a POI enabling the user to have a discussion on the situation without having to move outside of their apartment. The SVS allows three-way conferences with any POI, for example, a health professional, a family member, and a user.

The SVS can optionally have sensors (e.g. Near Field Communication token reader) to record when visits are done by a POI to the user. This information is maintained in a database. The profile of the POI may optionally be loaded on the SVS when they are visiting allowing them access to their contacts. Optionally, any POI can load their profile on the SVS in order to access their contacts and make call. The profile loading could be made by, for example, a pre-determine gesture on the POI's picture of the SVS. The SVS can optionally be used in kiosk mode, whereby the SVS is loaded with a profile (POI or USER) when an identification token is detected by a sensor. The profile is removed when the person walks away from the SVS.

The SVS incorporates touch screen technology, displays a set of fixed and predefined pictures on which a simple touch enables a video/audio connection to the desired POI The intent is to connect families in a very easy way and to address some of the social isolation issue for users. The SVS also enables virtual care and helps to limit health care professional visits saving time and money while offering more responsive service. The SVS is also a reference point for time, date, season, and reminder on health recommendation like time for drugs, and time for special treatment. The SVS is also transparently to the user a bridge for the telemetry and sensors technology. The data gathered from the SVS, is analyzed and acted on when needed to secure the environment. The SVS also comes with profile setting to enable more flexibility in configuration. In this case, a list of pictures can be used, with swiping to navigate, and on screen keyboard search. With a more flexible profile, the SVS allows instant message and emotions to be sent between a user and the POI.

The SVS generally comprises:
Touch Screen
Speakers
Microphone
WebCam
Ethernet connection
Radio: Zigbee®, Bluetooth®, WIFI®
Stand to support the SVS or wall mounted [0038] Optional output port to connect to larger screen TV [0039] Optional audio jack to connect to earphones.

The SVS is remote configuration by an admin including the selection a profile between full flexibility (for more experienced users) or simple experience (for the user).

Figure 3:
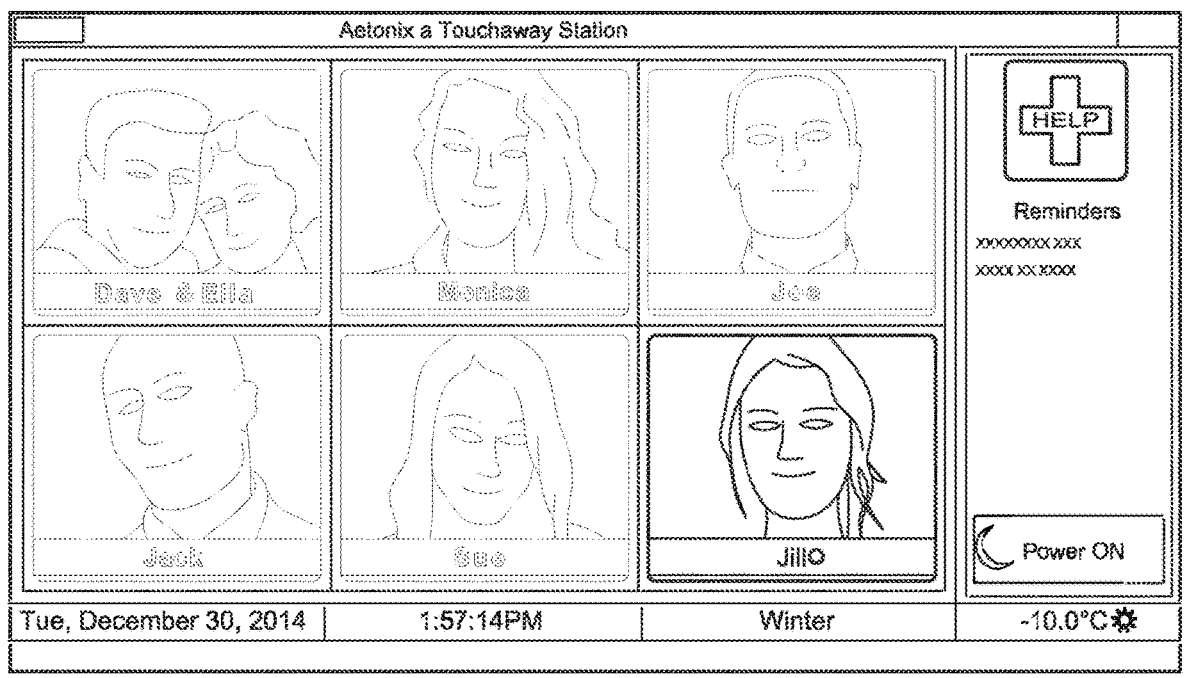
FIG. 3 is an example of an SVS screen.

In Simple experience profile, the limited functions available comprise:
 i. Selection of the POI to be displayed as people to be called
 ii. User login for the SVS (this map to the person using the SVS)
 iii. Pairing of the telemetry devices or sensors
 iv. Adjustment of date, time, and season
 v. Desire selection of display for availability
 vi. Time for emotion text to be displayed
 vii. Auto detection of faces with camera movement
 viii. Auto detection of voice alert
 ix. Auto detection of emergency call on SVS
 x. Configuration of emergency call (911 or health care staff)
 xi. Auto answer video/audio on call
 xii. Auto video/audio on emergency call
 xiii. Auto alert to specific user on emergency call
 xiv. Auto alert on certain biomedical/vital signs
 xv. Enable recording of video/voice message
 xvi. Language setup
 xvii. Configuration of temperature units In full flexibility profile (All the above and the following):
 xviii. All POI listed for a user are displayed and swapping is used to navigate
 xix. Enable keyboard access for Instant messaging & Emotions
 xx. Voice recording for message
 xxi. Continuous picture gallery display
 xxii. Internet browsing
 xxiii. Music players
 xxiv. Games support
 xxv. Instant video clip playing In simple profile, the SVS displays the pictures of the POI configured and allow selection for call. If a POI is not available, the photo is grayed out or disabled as shown in FIG. 3. If available, the photo is in relief and looks like a button that can be pressed. The photo also has the name of the person on it.

The SVS also allows for a POI to send emotion message to be displayed on SVS. A POI can optionally send a text or instant message that gets displayed on the picture for a configurable time. In the simple experience profile, the SVS doesn't allow for a reply to make it simple on users. In the full flexible profile, the Instant message & emotion can be sent from the SVS.

The SVS allows for call scheduling. The POI using the application can optionally schedule a video call with a user. At the scheduled time, an alarm is emitted on the SVS to notify the user that a call is about to happen.

The SVS also has voice recognition to allow connection through voice command. A user can initiate a connection by talking and mentioning the POI to be called or to place an emergency call.

The SVS always ensures a voice-only connection if bandwidth for video is not sufficient. The SVS has a Webcam that allow video capture and transmission. The webcam preferably recognizes facial movement and adjusts based on the position of the user.

Emergency call (911 or staff call) is placed if screen is consistently touched for a predetermined time. On an emergency call and if configured, the video turns on automatically. On an emergency, a list of desired POI can be notified of the situation. An alert can be sent to each of them.

The SVS has recognizes if a user has touched several times in few seconds a picture. This can be considered as a single touch. This allows for users with agility problem to use the systems (Parkinson is an example) effectively.

The SVS, on connection, displays the person been called in a quality size. Another touch on the end call button or the picture ends the call.

The SVS may be integrated with a fall/inactivity detection bracelet and calls an emergency automatically on fall detection or inactivity detection or simply when an emergency button press on the bracelet. The SVS generates warning and then alarm on the inactivity situation.

The SVS calls an emergency number automatically on vital signs alarm. Example, on a pulse change going lower than expected, the SVS calls an emergency number based on configuration.

The SVS also provides one or more reminders to the user. The reminder can be programmed remotely by a POI. Reminders can be scheduled in the future and optionally recurring. Reminders can be social activities, drugs and appointment.

The SVS can also support marketing message to provide the user with information on the product of its interest.

The SVS provides the user with reminder on the telemetry maintenance if required (e.g. low battery).

The SVS can receive video call and rings like a phone until it is answer or the caller hang-up. Display show the person calling in larger form with "Call received." The SVS answers. The SVS has the capability to record a video/audio message if enable and if phone not answer. The SVS has the capability to record a video/audio communication on a one touch on a record button while in a call. An animation may be played on the screen to remind the user how to activate the function.

If enabled at configuration time, the SVS displays in bigger form (bigger picture) when the user is near the screen with his finger but has not selected (touch).

The SVS allow incoming call from a POI even if it is not listed as a picture on the SVS, as long as it is in the list of the users. If not in the list, the SVS can optionally reject the call.

To avoid getting into complicated states, the SVS has a special approach to get into configuration mode. Touching bottom left corner of the screen for 7 times quickly bring the SVS in configuration mode. Any other combinations or times can also be used. The power down button can also optionally be disabled as well, the sleep mode can also optionally be disabled avoiding cases where the SVS is turned off or in a state that is difficult for the user to manage. As another embodiment, special gestures applied to the logo on the screen can enable different configuration modes.

The SVS supports remote debug/diagnostic, if enabled in the configuration. The SVS can have a software update remotely. Update can be scheduled at a preferred time using the configuration menu and is transparent to the user.

Optionally, the SVS keeps track of statistics. The SVS monitors which POI is called more often than other. This can be used to change the picture of the POI used on the SVS dynamically. Access to the log file can be done through the configuration menu. The SVS tracks the time spent on connection between a user and a POI to have history and trends.

The SVS, if enabled, allows display of the current telemetry on screen in place of some POI pictures.

The server 160 monitors one or more SVS to ensure they are always connected and in the proper login state. If connection is lost, the server notifies a POI or a system manager. If the SVS loses the login state, it retries automatically for a predetermined number of times before it sends a notification.

Remote control, configuration and updating of the SVS may use encrypted channels to avoid loss of personal information.

The SVS can optionally automatically answer a call to allow a POI to evaluate the situation by video with a user that is not answering a call.

The user optionally wears a wearable device referred herein as a wrist remote control (WRC) to enable remote control capability of the SVS. A call can be received and answered from the WRC enabling the video SVS to accept the call. The WRC can optionally be used to receive reminder (the same reminder that are available on the SVS). The WRC optionally allows a POI to detect falls based on its sensitive positioning device. The WRC provides an emergency call link to the SVS for immediate video capability and emergency call. The WRC optionally allows selection of a contact to call and initiate a call on the video SVS. The WRC optionally allows reception of a personal message from a POI (e.g. text message). The same message can be displayed on the video SVS. The WRC allow fall detection generating an alarm through the SVS to the POI. The WRC may also enable inactivity detection leading to warning and then alarm.

A WRC can optionally be used by the POI to, for example, receive emergency call and the biomedical data of a user, receive biomedical trend data for a user or receive reminder/tasks to be completed.

Figure 2:
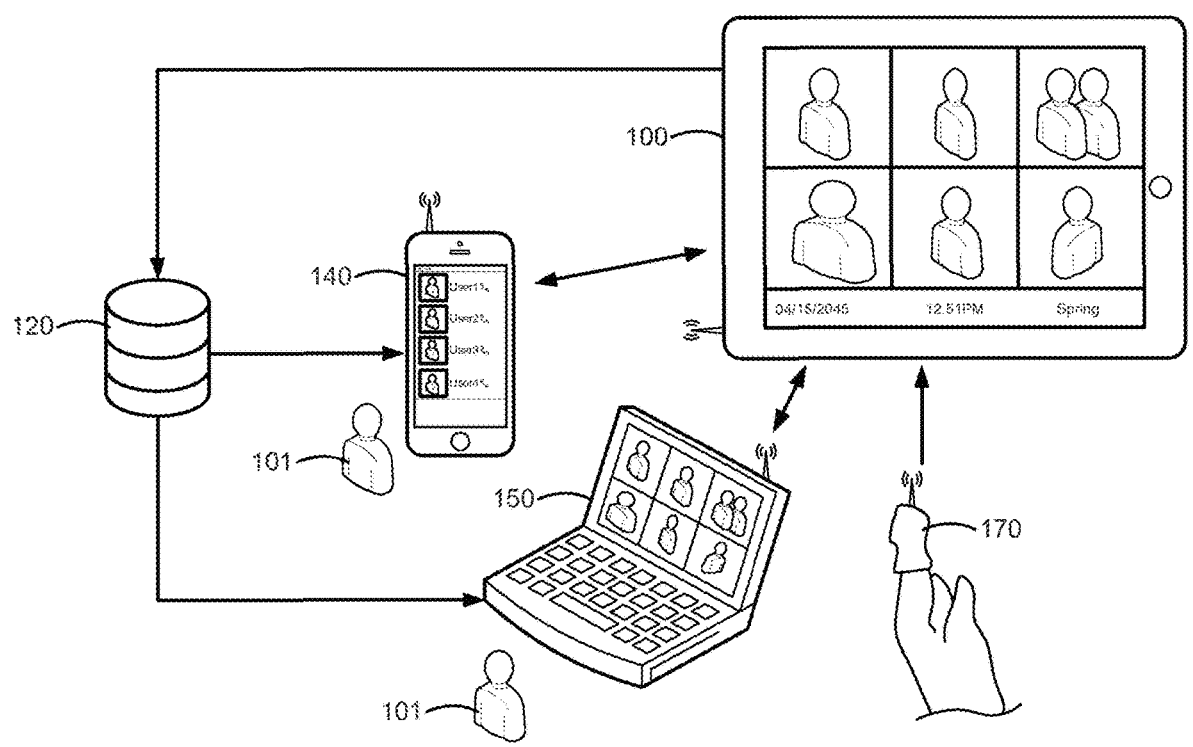
FIG. 2 is an example of the application structure.

The user of the SVS can communicate with another SVS or any other mobile phone or computer via an application used by a POI available through any application stores. An application is also available for download on a PC or Mac. FIG. 2 provides an example of applications running on computers 150 and smartphone 140 for POI 101. The user may wear a telemetry sensor 170 which communicates transparently with the SVS 100 to transmit the telemetry information which is stored in a database 120 and retrieved by the POI application 150, 140.

The SVS can be configured into a kiosk mode with a badge reader allowing a user to tag in have its profile loaded. When this is done, the SVS can be used by different users, for example in a library.

The SVS can optionally be setup into multi-users where a user selects their profile and login.

Application

The application is used to communicate between a SVS user and a POI. The application configuration management, through a web portal or on the device, comprises:
1. Selection of language
2. Creation/Configuration of the POI
3. Configuration of the POI and user list
4. Upload of picture for the POI
5. Login & password management
6. Creation of one or more group for one or more user for availability status for each group.

The application presents the POI with a user login screen. After the login action, the POI is presented with a list of users and other persons of interest with the associate pictures (see FIG. 2). The pictures are gray out or normal indicating availability or any other color combination showing availability. Gray out mean that the user or POI are NOT available. Beside each user or POI is a connect button, a texting message button, or telemetry button. If telemetry access is enabled, the POI can select the telemetry and see the history and current user data. With the telemetry enabled, the POI can be notified of alert if configured in the SVS.

The application allows the user or POI to define availability per user, per group, or for all. This is useful in the case that a user keeps calling back due to memory challenges like Alzheimer. The POI logoff or set is availability status to unavailable if this is necessary. In another embodiment, a timer may be configured for each POI and the user is prevented from calling back a POI if they just completed a conversation earlier than the expiry of the timer.

In order for the SVS, or application, to connect between users and POI, a communication server is required. The communication server can be the same server as the configuration server or a different one. It can be centralized or distributed. A server with all user and POI is provisioned and refreshed regularly or each time a new user or POI is added. The concept of "user in the cloud" is used. Anyone using the application or the SVS has a user identifier and password and a picture. The profile of the user or POI is stored in a configuration database 125.

If a connection needs to be established, the server signals the connection and sets up a peer to peer direct connection between the user and POI.

Optionally, the data related to telemetry is stored only for a maximum of days of history. Optionally the telemetry database is located on private network and secured with encryption.

In order to establish connection between two SVSs or with an application, the system needs to go through a signaling process. After signaling completed, the peer to peer video connection is established. Prior to that, a server in the cloud (the configuration server) does the mapping from one user to the POI. The user initiating a call has a communication identification (commID). This commID is pushed to the server. The users or POI that are logged in all have a unique commID. The signaling handles the connection between the originator of the call and the recipient of that call. When signaling is completed, a connection gets established, and then a peer to peer connection takes place with video and audio. The server can be a public (e.g. Google.® server or a private one. The protocol WEBRTC is an example of an open source software platform that can be used. Any other protocol that interoperates between any platforms can be used.

Telemetry/Sensors Platform

The SVS is designed to enable connectivity with telemetry equipment and sensors that can communicate through Zigbee® or Bluetooth®. Any wearable Biomedical devices or any in room telemetry or sensors equipment that comply to the API of an open platform, can be connected to the SVS and have the data transferred to the user database and be stored/analyzed by qualify staff The remote configuration of the video SVS, allows administrator to add protocol compliant telemetry or sensors equipment.

The SVS has alarm detection, which flags issues with telemetry data as configured to one or more POI. With the telemetry data transferred to the network, POI can review to identify anomalies. The system can also be configured to notify POI of unexpected behaviors. As example, an irregular pulse can trigger an alarm. Another example is an element open on a cook top for long time can trigger an alarm if some telemetry is in place for monitoring such event.

The telemetry data is transferred on a continuous basis while the user is collocated with the telemetry sensor and the SVS. When outside of reach, the telemetry sensor may buffer the data in memory until the next available time of connectivity with the SVS.

The SVS, with the telemetry information, may report to POI the mood of a person. Using heart rate, temperature trends, and potentially body humidity level, the system indicate to the POI how the user is doing and if the person is suitable for a call in the case where the person may be limited by cognitive impairment. The feature helps with ensuring that a call is made to a user when in its best condition. The POI is optionally notified by a red, yellow, or green status light on the application.

The SVS is pushing continuously data to a server and database for storage and analytics. The server can analyze trends per user for each telemetry items and based on notification configuration, notified POI if undesired situation happen. The server can also do some data mining, some pattern analysis, and provide with potential warning of human changes or environment change. The data trending, mining observation, and notification are store in the database and can be accessed by POI to analyze and provide recommendation to a user.

Since the data is per user, it is possible to configure that one or more POI, access at the data. Family can maintain a close status on users. The data is useful for health staff like doctors to see trends and behaviors to diagnose a situation.

The servers and database can be implemented as a stand-alone system for a residence or cloud services where the servers and databases are offered remotely as a service to the residence. A residence may decide to have a server infrastructure local and have the data private while the communication is still possible.

Since it is also important for residence management to monitor staff interaction with resident (user) and to ensure that face to face service is offer, telemetry/sensor are used to monitor visits to each apartment. The badge reader or identification card can connect to the SVS and push information on visit time and staff identification. This way information per staff and per user is available to management to improve its service if required. It is also extremely useful for audit as the data is available and reports can be issue with the administrative application.

An administrative application is available to selected POI.

From the administrative application, several functions are available:

a) Administrator: This professional can add or delete user or people of interest. It can enable debugging, or network performance monitoring. It can configure databases and servers. He can set privilege for other user. It has access to all system data. The admin can also configure a SVS and force a reset of configuration of a SVS.

b) Health Specialist: This professional has access to all user data and can use trending, data mining, history, and current data. This professional can set new threshold or alarms for a given user. This professional can set the reminders and the schedule of the reminders. This professional can request from administrator a reset of the data.

c) Management: This professional has access to statistics, and report on user interaction but does not have access to the private data except if allowed by a user and the health specialist. This professional has access to all staff data and interaction with resident. He can set notification alarms for staff scheduled visits with resident and ensure that they are done. This professional can print report for audit purposes.

d) Staff Support: This professional provides assistance to the user to setup the telemetry. They have access to server to ensure that telemetry data is active. This professional also received telemetry alarms like battery low, malfunction, and can take action to repair telemetry. This professional also gets alarms on environment telemetry like water leakage or cook top open. In this case, the professional can take immediate action. This professional can add user or person on interest remotely. A SVS can be programmed remotely with the expected configuration and list of POI. Typically this professional helps in setting up the SVS after the sales of the service.

The administration application allows to input manual data by hand to the database for each user. For example, data from a visit can be stored per user based. This data can be used by health specialist and can be report on.

Figure 4:
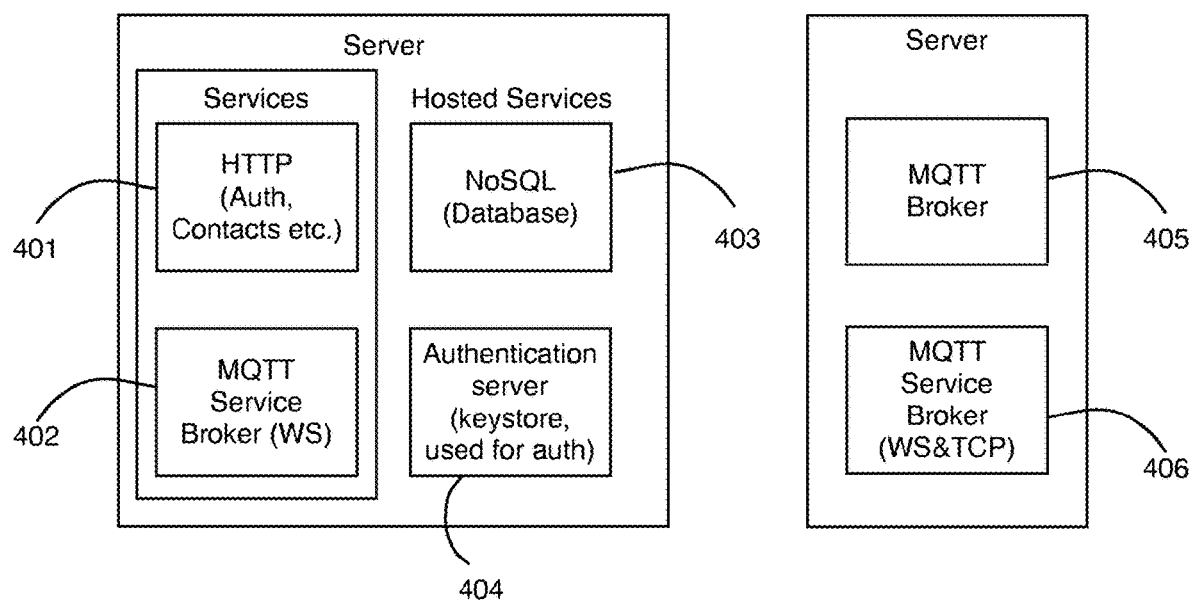
FIG. 4 depicts an example of the modules used to deploy simple point-to-point video where multiple applications are distributed on one or more servers.

FIG. 4 depicts an example of the modules used to deploy simple point-to-point video where multiple applications are distributed on one or more servers. The embodiment includes a document oriented database and a key value store (type NOSQL) 403, an authentication server to control access 404, a Message Queue Telemetry Transport (MQTT)

broker server 405 used for messaging between processes for websockets and TCP/IP sockets.

The HyperText Transfer Protocol (HTTP) module 401 enables HTTP request to get contact list, device setting, and information on contact invitation for the SVS. All device type could emit an HTTP request to get information from the server.

The MTTQ service broker 402 provides SVS with an Application Programming Interface (API) that enables desktop applications or IOS applications and SVS station to send/receive MQTT messages to/from other devices in the network. The API is a custom broker built with an open source library. The broker 402 also performs authorization and request for authentication.

The MQTT Android service broker 406 provides SVS with an API that enables Android app to send/receive MQTT messages to/from other devices in the network. The API is a custom broker built with an open source library. The broker also performs authorization and request for authentication.

The database 403 enables the SVS platform with a document and graph type database (NoSQL). The database maintains all administration information about the users, status, preferences for the system, preference of type of call, contact list, pictures, voice mail, video messages, logs on users about health.

The authentication server 404 provides a server mechanism to authenticate any access to data. It is used for MQTT message and HTTP request. Any failure to comply causes an error of authentication and data is not accessible.

The MTTQ broker 405 is an open source library. This container of software enables messages to be created, delivered, and diagnosed. The WebSocket and TCP brokers are communicating with the MQTT broker for messages.

Figure 5:
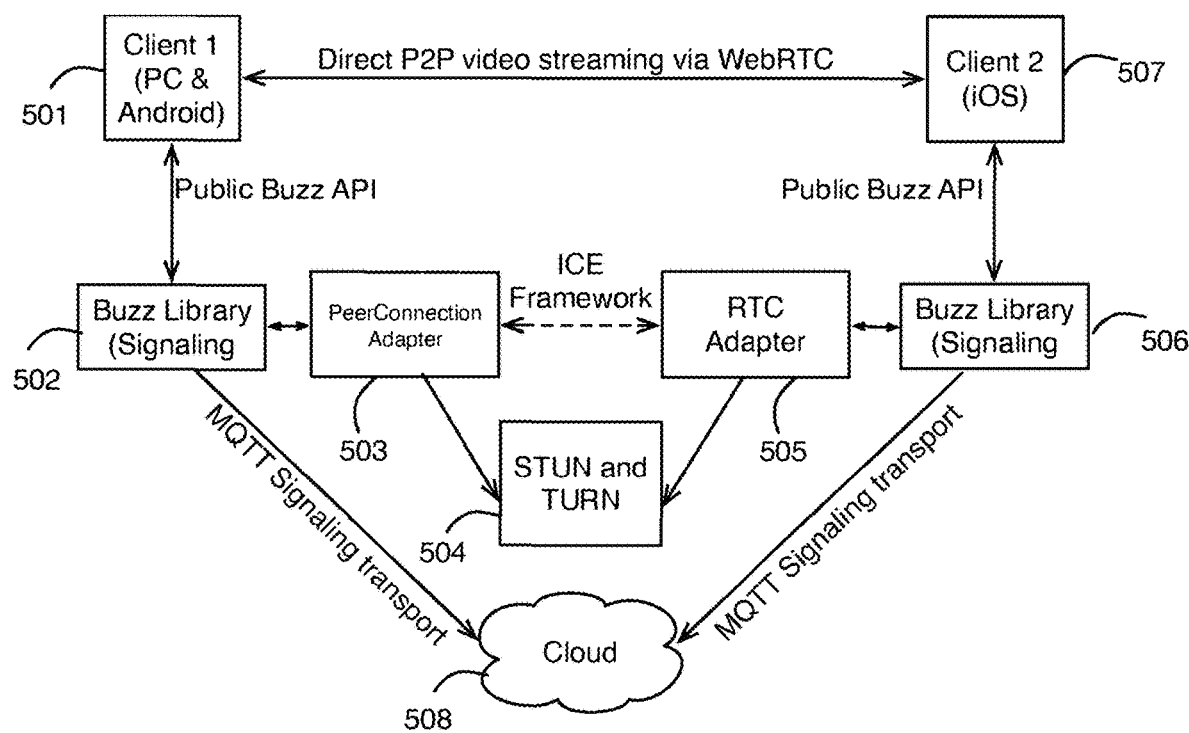
FIG. 5 provides an overview of the call flow between 2 clients.

FIG. 5 provides an overview of the call flow between 2 clients. The buzz library enables signaling between the clients using the MQTT transport layer. Messages are exchanged until protocol agreement. RTC is then used over the Internet Communication Engine (ICE) framework to establish the peer to peer (P2P) connection path. When done, the client communicates over P2P. Session Traversal Utilities for Network address translation (STUN) and Traversal Using Relays for Network address translation (TURN) servers are used into the P2P connection to overcome firewalls and routing issues.

A device 501 of a user establishes a peer to peer video audio call. The SVS application running on the device presents an interface to the user to make its call and interact with the signaling engine library through the SVS public API. On user request, like pressing on a call button, the SVS device application executes the proper algorithm and call APIs of the signaling library to start the process of a call.

The SVS application running on an user device, include the signaling library 502 which enables the application to signal the far end device through MQTT messages to setup a connection. The signaling library 502 algorithm takes care of identifying the room ID for the communication, gets authorization to communicate from the servers, prepares the adequate MQTT message with the ID of the callee, and sends the required messages. The signaling also takes care of the reception of a request for a call. The signaling library 502 acknowledges a request. Finally, the library 502 also exchange on the Session Description Protocol (SDP) and the ICE candidate to be used for the communication between the 2 users. Any message been sent from the library is sent on the cloud (Internet) with the proper destination address. After the signaling phase is completed and that the room could be joined by both user's device, the signaling library proceed with establishing a peer to peer direct connection by using the "Peer Connection Adapter" represented in FIG. 5.3.

The PeerConnection Adapter 503 provides the SVS system with an abstraction layer of the WEBRTC primitives. The simple API enables the signaling library to establish, or close calls very easily. When a communication is established between 2 devices, the ICE candidate establishes the direct P2P streaming via WEBRTC. It also enables error handling and fault detection. The adapter is not available for IOS devices.

The STUN and TURN component 504 of the SVS systems handles discovery of IP address behind firewalls and routers. The STUN is a standardized set of methods and a network protocol to allow and end host to discover its public IP address if it is located behind a network address translator. TURN is a protocol that assists in traversal of NAT or firewalls for multimedia application. Adding this component 504 into the SVS system ensures that an IP is known and reachable.

The SVS system may comprise an RTC Adapter for iphone Operating System (IOS®) 505. This adapter provides equivalent function of the PeerConnection adapter 503 for Android and PC. This abstraction layer provides access to the WEBRTC primitive on IOS. The RTC phone adapter also provides an API that enables the signaling library to establish, or close calls. When a communication is established between 2 devices, the ICE candidate is set and used to establish the direct P2P streaming via WEBRTC. It also enables error handling and fault detection. The adapter is only available for IOS devices An IOS signaling library 506 is used for IOS connections.

Devices communicate over the internet 508 for their private P2P video/audio call.

Figure 6:
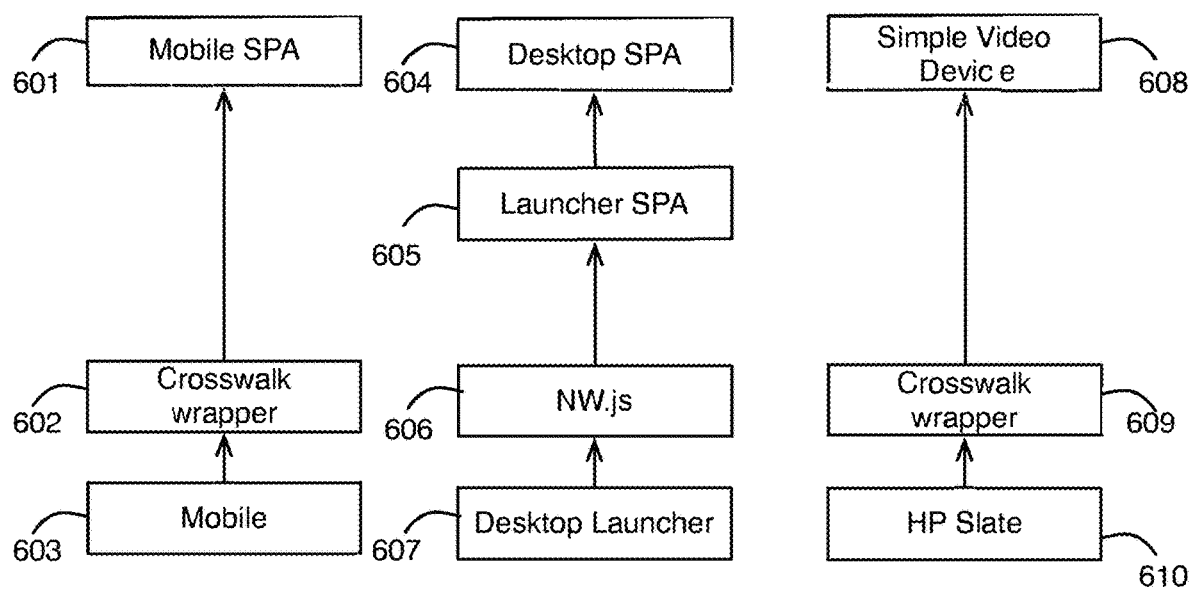
FIG. 6 is an example of a Single Page Application (SPA) approach used for the smartphone, hub and simple video device.

Referring to FIG. 6, a Single Page Application (SPA) approach is used for the smartphone, hub and simple video device. For mobile Android or the simple video device, a Crosswalk wrapper is used. For IOS devices, another RTC platform is used, and for the desktop, a Node webkit is used along with a launcher page.

A Single WEB Page Application (SPA) 601 for the mobile device is used to create mobile content using, for example, the Crosswalk wrapper for the Android devices. Support for HTML5, CCS3, Javascript is available.

The crosswalk wrapper 602 is a simple implementation of a Crosswalk library for the SVS systems for the android devices. It enables the application to run, for example, HTML5, Javascript, and CCS3.

The SPA is executed on a mobile device 603.

For desktop, a Single WEB Page Application (SPA) for Desktop device (MAC and PC) 604 is provided. The web content is created using the NodeJS webkit. Support for HTML5, CCS3, Javascript is available.

The launcher of Single Web Page Application 605 checks if new content/new version is available from the content server and refresh with the latest at start time of the application.

A public source code such as NW.js 606 enables to develop fast, scalable network application like SVS. This platform builds on Chrome's javascript runtime. Any other platform with similar functionality can be used.

A desktop launcher 607 launches the execution of the SPA on the PC or MAC.

For the SVS 608, a Simple WEB Page Application (SPA) is created using the Crosswalk wrapper 609 for the Simple Video device. Support for HTML5, CCS3, Javascript is available. The SPA is executed on a video device 610 with optionally reduced capabilities.

Figure 7:
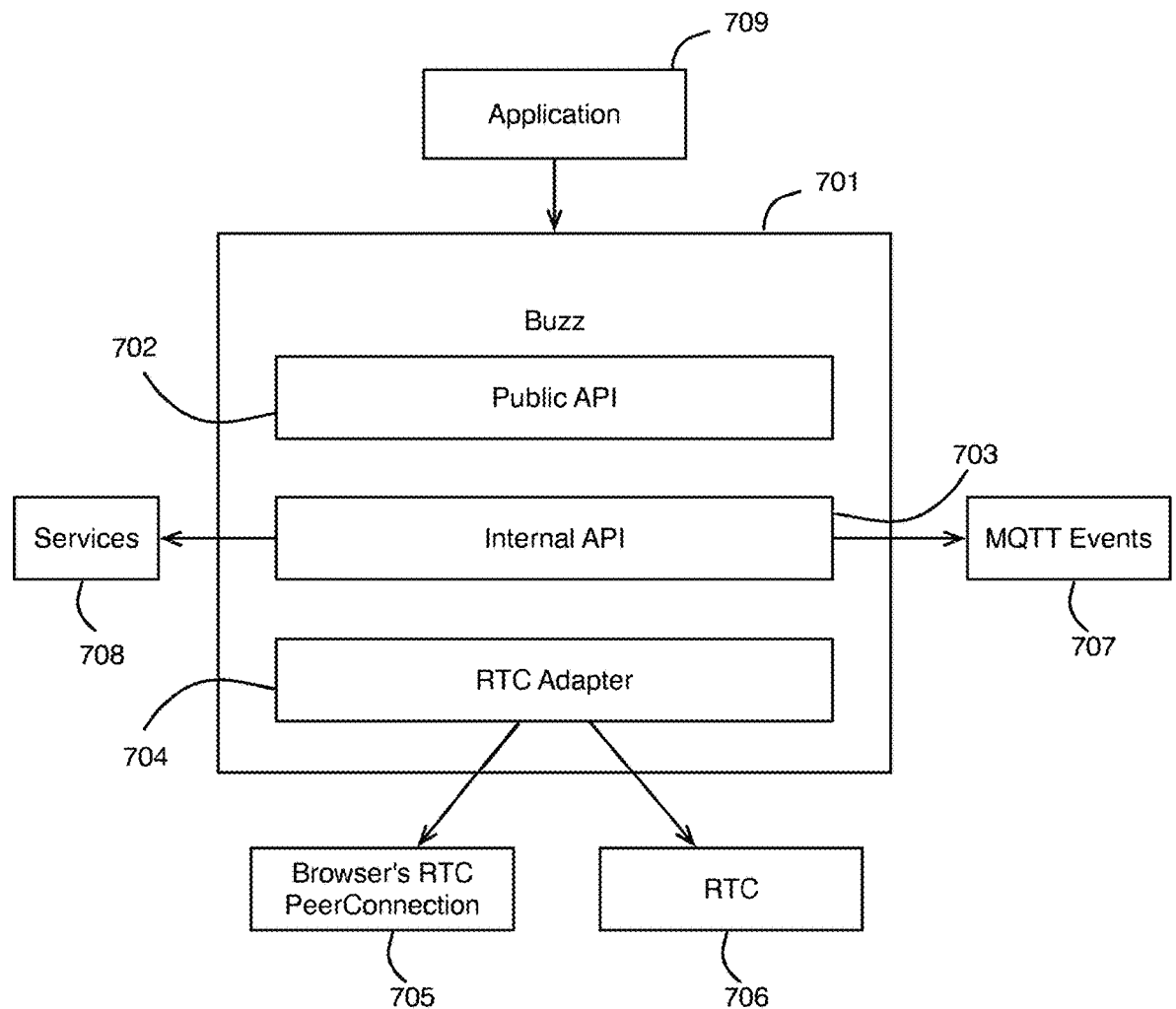
FIG. 7 shows how a signaling library is used to establish peer to peer connection between users.

In FIG. 7, a signaling library 701 used to establish peer to peer connection between users. Its public API enables the application 709 to manage calls between remote device and itself The library has an internal API 703, a public API 702 and has an RTC adapter 704 facilitating the use of RTC 706 for P2P 705. The library uses MQTT events 707 for discovery of actions to be taken and uses services 708 to send messages, get authorization and authentication, and to send HTTP requests.

The signaling Library container 701. The library has a public API used by the applications, an internal set of API, and provides an RTC adapter to connect to RTC PeerConnection for IOS and PC or to RTC adapter for IOS.

The Public API 702 is used by the application to establish a call with a user on a different device. The Internal API 703 is used by the signaling library. This is only used internally.

The RTC adapter 704 of the signaling library creates an abstraction to the specific RTC layer for each device.

The signaling library 701 registers to listen to events that happen with the delivery MQTT messages 707. When a message is delivered, MQTT events are raised to enable the signaling library to take action.

The signaling library is taking advantage of several services 708 offered. The service for authentication or authorization is provided to the signaling library. Service of registration and database access is also available. Any other services may be offered to the signaling library.

Figure 8:
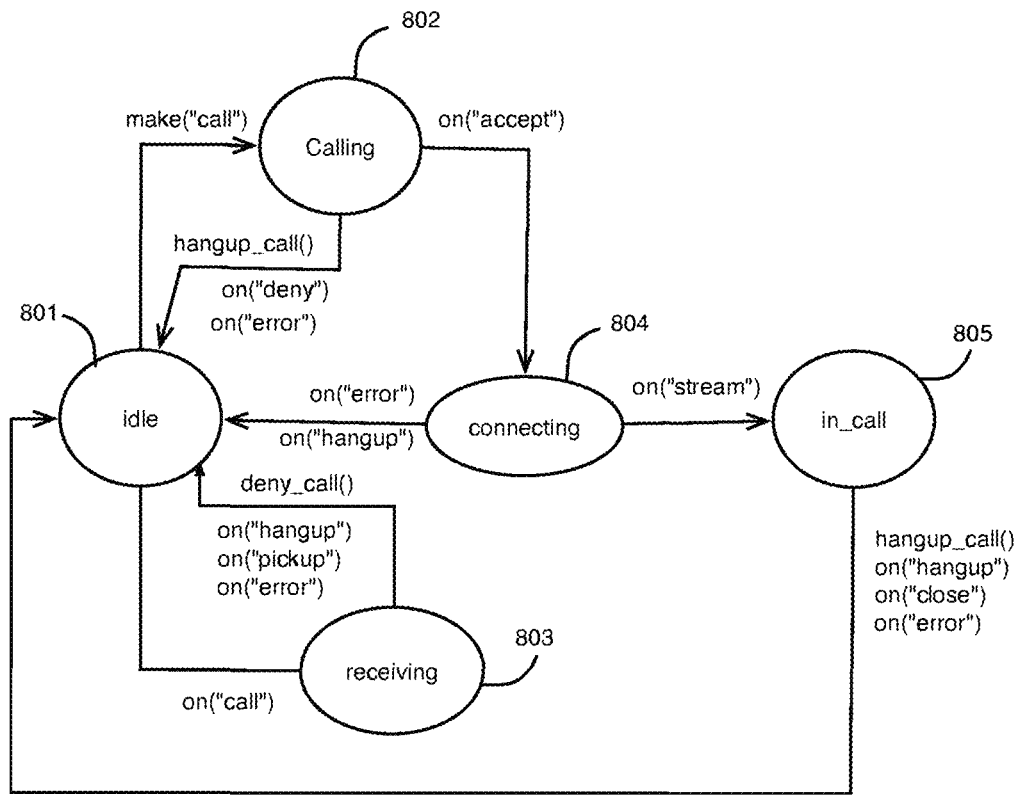
FIG. 8 shows an example of the state machine for establishing a peer to peer call between devices for the SVS system.

FIG. 8 shows an example of the state machine for establishing a peer to peer call between devices for the SVS system. Five states are enabling the SVS system devices to take the proper actions. Many of the state transition are due to MQTT message exchange between two devices based on the action of the user.

The initial state 801 of the application on a device is the "Idle" state. In this state, no call has been initiated and calls could be received or made.

The "calling" state 802 of the application represents that a user on a specific device using the SPA has trigger a call by pressing the call function. The API make_call( ) will transition from "Idle" state to "Calling" state and the proper MQTT message to be sent to the far end. If the user select the hang-up call function or an error happens or the far end user denies the call, the state machine for this device returns to "Idle" state. If the far end user accepts the call, the process of signaling starts and the SVS device transitions to "Connecting" state.

The "receiving" state 803 of the application represents a user receiving a call on its device from a remote user. The application moves to this state based on a MQTT message received. If the application is in idle state and a "call" message arrived, the state machine moves to "receiving" state. While in "receiving" state, if the user accept the call, the application for the moves to "connecting" state. In the case that the call is deny by the user the state moves to "Idle." If the far end user stop calling (hangup) than the state moves to "Idle." If the user receiving the call, answer the call from a different device, the current device SVS state moves to "Idle." Finally error message on connecting moves back to "Idle".

The "connecting" state 804 for the represent the period in time where the connection is getting establish. The signaling is getting done and the WEBRTC peer to peer is getting setup. Assuming a successful connection, and the video stream is available, the SVS system moves to "in_call" state. If an error happen while connecting or if one of the user hangup, the state moves back to "Idle".

The "in_call" state 805 is the desired state for ensuring that a call is in progress and the application is connected in VIDEO/AUDIO with another user. If any of the user hangup, or if connection failed, the SVS state moves back to "Idle".

Figure 9:
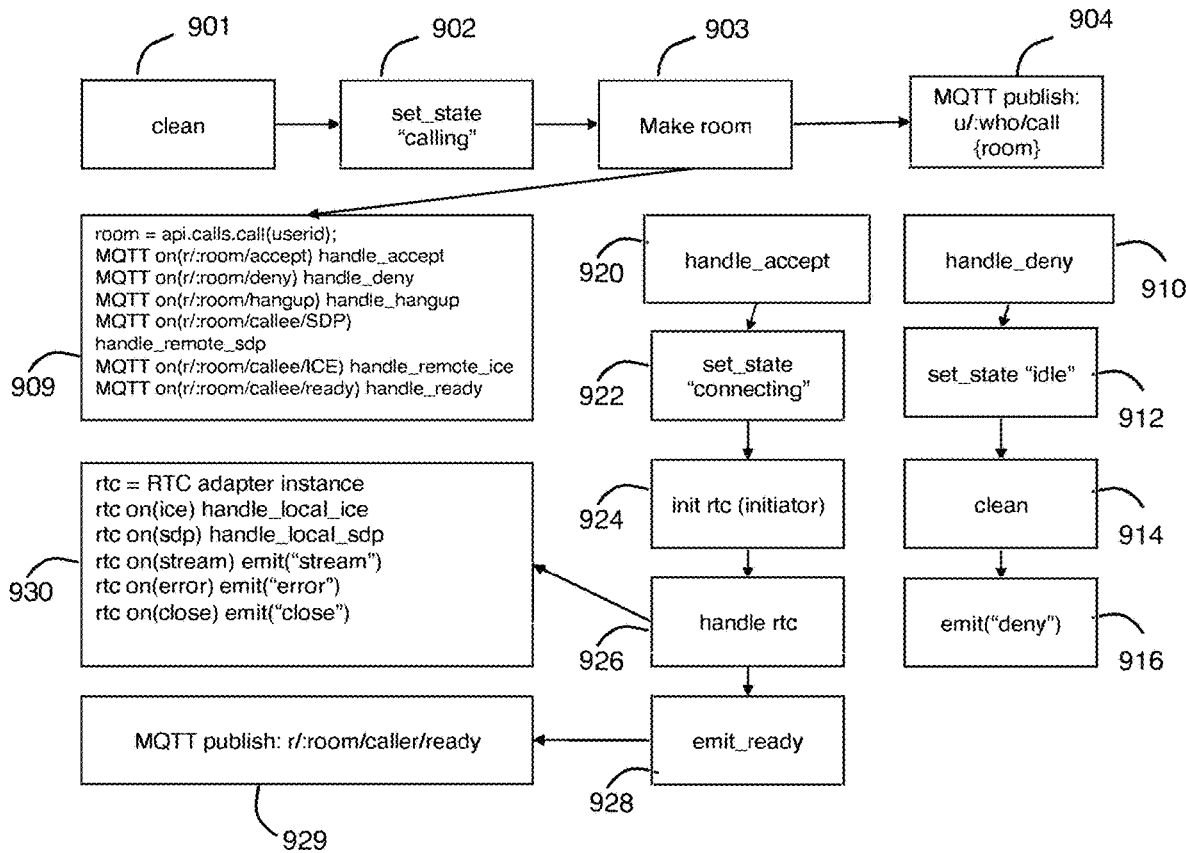
FIG. 9 shows an example of a call is being made between 2 devices.

FIG. 9 shows an example of a call is being made between 2 devices. The first step is done is to clean the current state 901 of the state machine to make sure that the previous call's data has been freed from memory. When this is completed, the state is set to "calling" 902.

After the cleaning activity has been completed, the process will proceed on creating a new communication "Room" 903 by calling a server API. Then it starts listening on MQTT events related to the room and to the callee. The MQTT messages are as followed 905:

room=api.calls.call(userid);
 MQTT on(r/:room/accept) handle_accept
 MQTT on(r/:room/deny) handle_deny
 MQTT on(r/:room/hangup) handle_hangup
 MQTT on(r/:room/callee/SDP) handle_remote_sdp
 MQTT on(r/:room/callee/ICE) handle_remote_ice
 MQTT on(r/:room/callee/ready) handle_ready The SVS system sends an MQTT message to the callee 903 with the room information and who the call is from. The form of the message is MQTT publish: u:/who/call (room).

The SVS system handles calls to be denied 910. If a callee denies the call, the state is set to Idle 912 for the caller, the state is cleaned 914, and the rest of the applications receive a deny event 916.

The SVS system accepts the call 920 by setting the state is set to "connecting" 922 and the RTC connections is setup 924. The room get notified that the caller is ready for sending RTC information 926 by "emit function" 928: MQTT publish: r/:room/caller/ready 929.

A new RTC adapter is created 930 and set to be initiator of the call. Listeners are added for various events from the adapter. The RTC messages are: [0173] rtc=RTC adapter instance [0174] rtc on(ice) handle_local_ice [0175] rtc on(sdp) handle_local_sdp [0176] rtc on(stream) emit ("stream") [0177] rtc on(error) emit("error") [0178] rtc on(close) emit("close").

Figure 10:
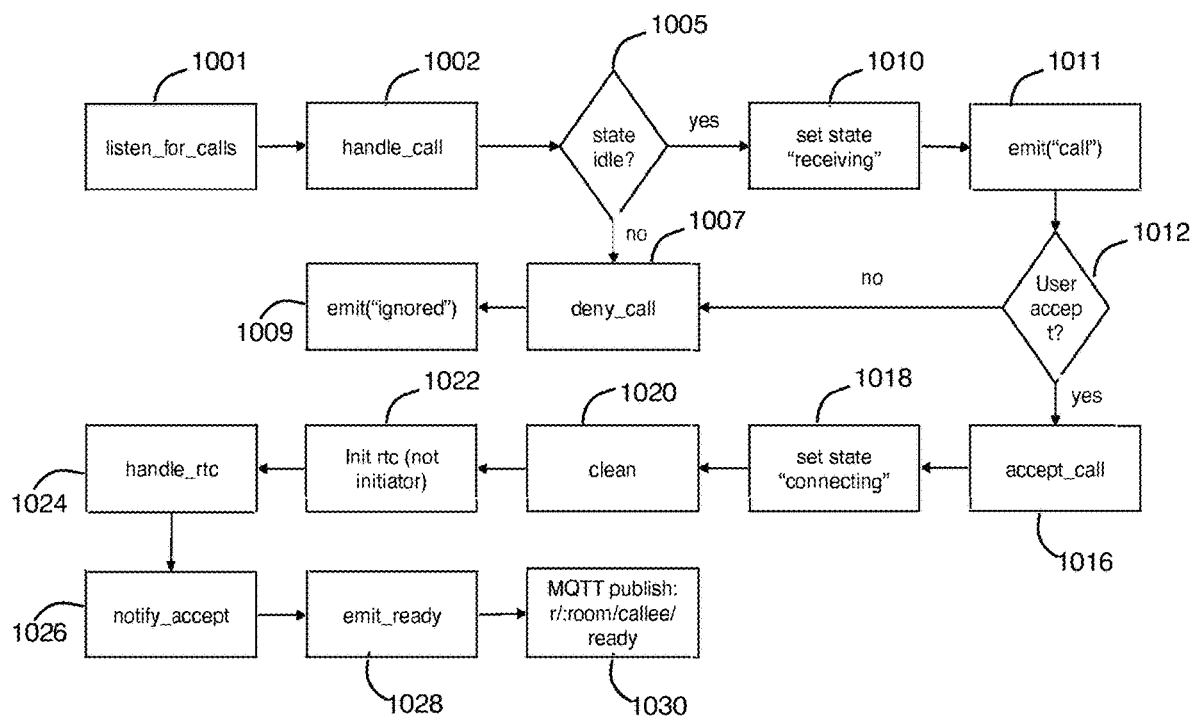
FIG. 10 shows an example process for a device to receive a call from another user.

FIG. 10 demonstrates the process for a device to receive a call from another user.

When the application on a device of the SVS system first boot, it subscribes the MQTT topic for incoming calls 1001. Once data is published to that topic, it is processed as a new incoming call 1003.

The application on the device is listening for calls 1001. Whenever a new call arrives 1002, the application checks to see if it is currently in the idle state 1005. If the state of the device is not in the "Idle" state 1007 when a call is received, then the call gets denied and the caller gets a message over MQTT informing that the call is rejected 1009.

If the state of the device is in "Idle" state when a call is received, the state get set to "receiving" 1010 and the user get prompted 1012 to accept 1016 or deny the call 1007 through the proper presentation layer of the user interface. If the user denies the call using the SVS system 1007, than the same process as above is performed.

If the user accepted the call 1016, then the state is set to "connecting" 1018, the state is cleaned 1020, the RTC adapter is created 1022, events for the adapter are listened on 1024, the caller is notified that the call has been accepted 1026, and the callee emits an event to the room 1028 saying that they are ready to exchange the RTC communication data 1030.

Figure 11:
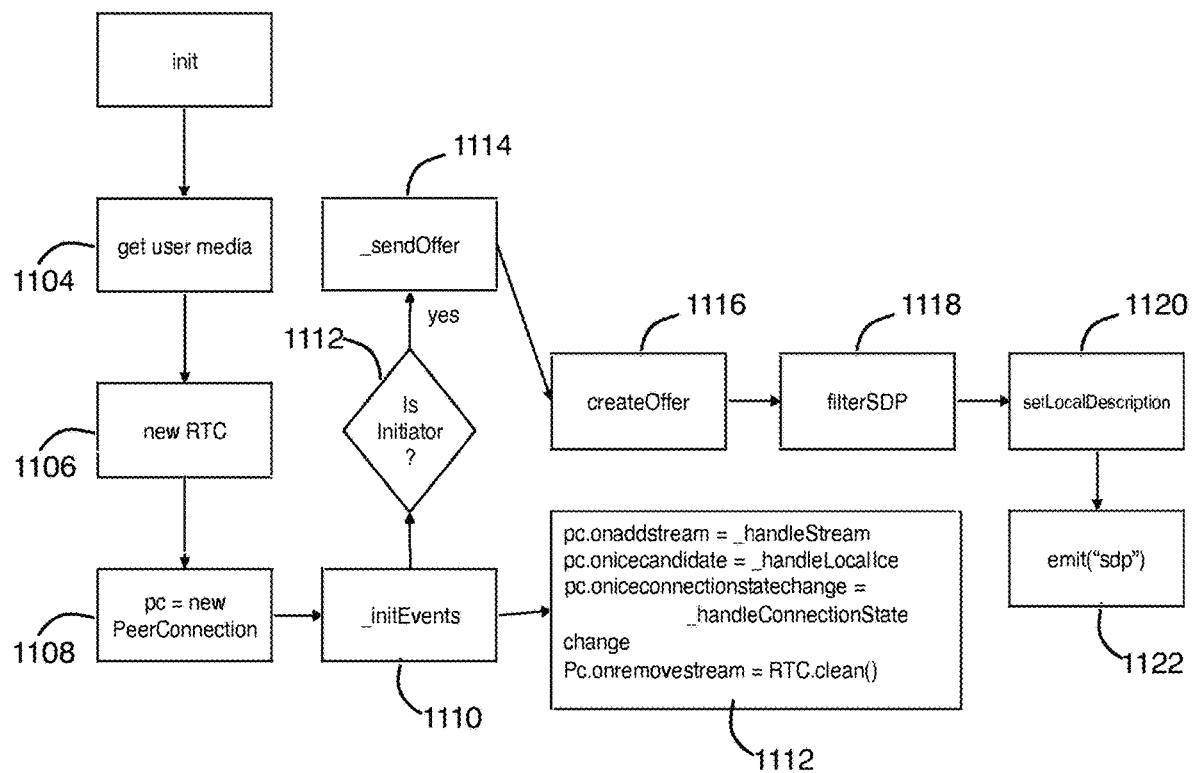
FIG. 11 describes the process of setting up RTC adapter in desktop browser.

FIG. 11 describes the process of setting up RTC adapter in desktop browser.

The desktop application gets the camera/microphone media stream 1104, creates a new RTC instance 1106, and attaches a new PeerConnection instance of RTC adapter 1108.

The SVS systems can add listeners 1110 to the PeerConnection to handle receiving new media stream, ICE candidate, and SDP data. It also handles closing and cleaning the RTC adapter 1112.

If RTC adapter has been setup as the initiator of the call 1112, the adapter creates the initial SDP string and sent it to the client 1114. The SDP string of the initiator's machine is created 1116. The SDP string describes the video/audio formats that are supported (bitrate, resolution, compression etc.). The SDP settings are modified 1118 to give more fine-grained customization of the SDP parameters for further optimization. The local SDP string is set 1120. The SDP string is emitted and sent via MQTT to the callee 1122.

Figure 12:
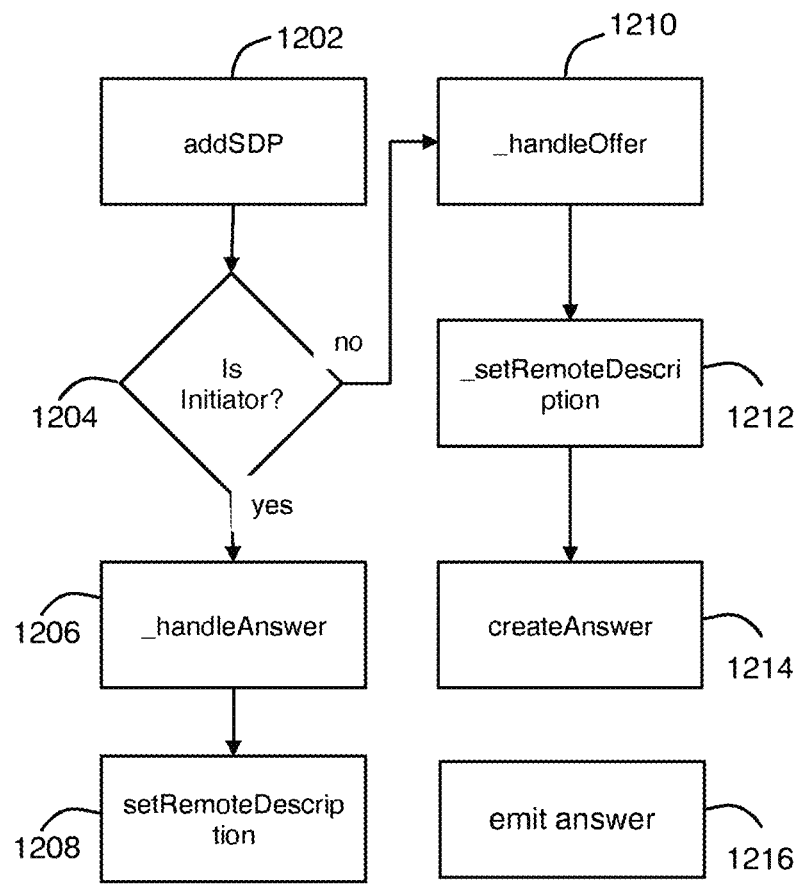
FIG. 12 describes the process from the application running on a desktop and receiving call information from another device.

FIG. 12 describes the process from the application running on a desktop and receiving call information from another device. SDP information is received 1202 from the other device and it is received over MQTT. If the RTC adapter is the initiator 1204, then it processes the SDP as the "answer" 1206 and set the remote description of the PeerConnection 1208.

If the RTC adapter was not set up as the initiator 1204, then it processes the SDP as the "offer" 1210, set the remote description 1212, then generates its SDP answer 1214 and emit the answer to the application to be sent over MQTT 1216.

Health Indicator Monitoring

It is in the interest of the user to track his/her health information in a manner which is simple. Non-limiting examples include activity (step count), blood sugar, blood oxygen saturation, body temperature, pulse oximetry and heart rate, and weight. Such information ("health indicators") may be collected by way of one or more biometric telemetry devices, or input manually by the user. The results are displayed to the user on the SVS and may be displayed to the one or more POIs.

In addition, in some jurisdictions, collection, storage and dissemination of such personal health data may be required to abide by privacy legislations. For example, in some countries, personal biometric data collected from a device must be stored at a physical location (e.g. datacentres) within that country. The same applies to data collected manually. In situations where privacy legislation is in place, the data is input directly to the SVS and then transmitted to the database 120 via network 110 (shown in FIG. 1). In these instances, the biometric telemetry devices comprise means for a wireless communication standard (e.g. Bluetooth®, Zigbee®, or any other wireless communication standard know in the art) with an open interface.

Alternatively, where such legislation is not an issue, the data may transmitted to a cloud first, and then transmitted, via authentication, via network 110 to database 120.

The SVS is configured to allow for manual input of biometric data, or to interface with one or more biometric telemetry devices. In order to simplify the process of taking a reading using the SVS, the user activates a protocol of the SVS. Such activation may include touching a button icon on the SVS screen. If a biometric device is to used to provide data for the health indicator, the SVS application dynamically determines how to communicate with the appropriate device based on known device names. A simple interface is provided for showing visual features (for example, graphs, charts, etc.) of trends for the user's biometric data. Optionally, a summary of the results can be shown to the user. For example, this may include a weekly summary of their daily results; a monthly summary of weekly results, or any other suitable format. In addition to accessing the biometric data, the user interface can also control who in the list of POIs accesses or sees the biometric data.

The biometric data is stored on database 120 for later viewing and/or for sending real-time updates to one or more active viewers (i.e. POIs) of the data.

The infrastructure for permission management (between POI 101 and the network 110) may be used to control which POI may have access to one or more of the user's health indicators. As such, each authorized POI is able to see one or more summaries, or updates of a user's health indicators after the readings have been taken. Alternatively, the authorized POI may see the readings in real-time, since as soon as the user takes a health indicator reading, it is pushed to each logged-in POI that is authorized to see it.

The devices for monitoring of health indicators are distinct from the fall detection bracelet. A few of the key differences are as follows. A main purpose of the WRC is to continuously monitor users so that people immediately responsible for their care are immediately alerted when a negative event occurs (e.g. a fall). This, for example, would be a POI within a facility where the user is located.

As such a user is always wearing the WRC, which is always be turned on and connected to a tablet (e.g. SVS). The user's urgency contacts are notified if the WRC is disconnected from the tablet (e.g. battery runs out, user wanders away, etc.). A user can press a button on the WRC to call for help from facility staff; the WRC automatically notifies facility staff when the user falls down. Furthermore, within a facility (e.g. a nursing home), tablets may collaborate in order to connect to bracelets for users anywhere in the facility and relay events to the patient's main tablet. Furthermore, each user has a unique WRC "assigned" to them by saving the bracelet MAC address to their account. A history of falls/urgency calls is not shared with the circle of care (i.e. all of the POIs), but only that POI (i.e. management) which is within the facility.

Conversely, the devices used to monitor health indicators are not used (or turned 'on') until the patient requests a reading. An exception may be a step counter, which is usually affixed to the patient and is continuously taking step readings. Furthermore, not all of the health indicator types have device integration—as described below. Data can be manually entered from non-Bluetooth devices. In addition, a user does not need the hardcoded MAC of a device in order to connect to it. Instead of using the multi-tablet scanning approach for fall detection bracelets, a simply scan for nearby devices with the appropriate name is performed for monitoring of health indicators. Multiple types of data (e.g. weight, blood oxygen, pulse, etc.) is collected through health monitoring. Finally, any number of the POIs can gain permissions to access data for a given health indicator and see trends on the data.

Figure 13:
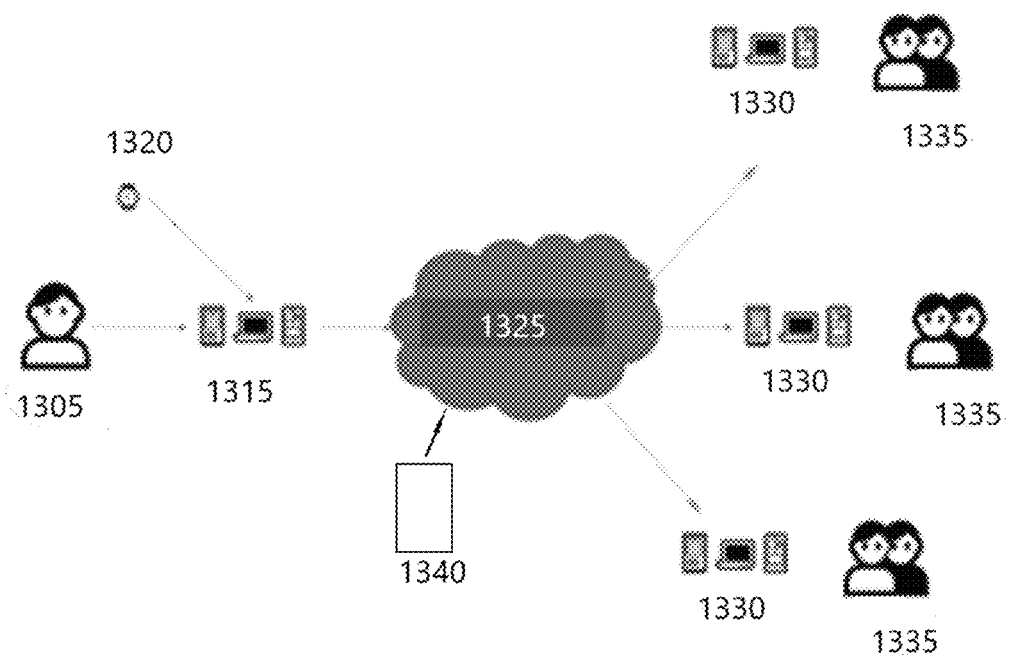
FIG. 13 illustrates an overall architecture of an embodiment of a system for collecting, storing, manipulating and disseminating biometric telemetry data collected from a user.

FIG. 13 illustrates an overall architecture of a system 1300 for collecting, storing, manipulating and disseminating biometric telemetry data collected from a user.

The user 1305 interacts with the application on his/her SVS 1315 (e.g. laptops, desktop computers, tablets, phones, etc.). The application on the SVS 1315 guides the user 1305 on how to take one or more readings using the device 1320.

Alternatively, the application on the SVS 1315 guides the user on how to enter biometric data manually.

The biometric telemetry data is sent to the SVS 1315, and processed so that it is presented in an easily-readable form for the user. The data sent is then via the application to the database 1340 (which may be stored in a cloud 1325). One or more of the POIs who is authorized to access the health data, can check to see if new health data has been uploaded to the database. Processing may include conversion to a certain format; conversion of units, etc. The one or more POIs 1335 each use the application 1310 on his/her individual device 1330 (laptop desktop computer, tablet, phone, etc.) in order to view data from the user 1305. The one or more POIs 1335 may then address changes in the observed biometric data by getting in touch with other POIs, the user and/or update any medical records of the user 1305.

Figure 14:
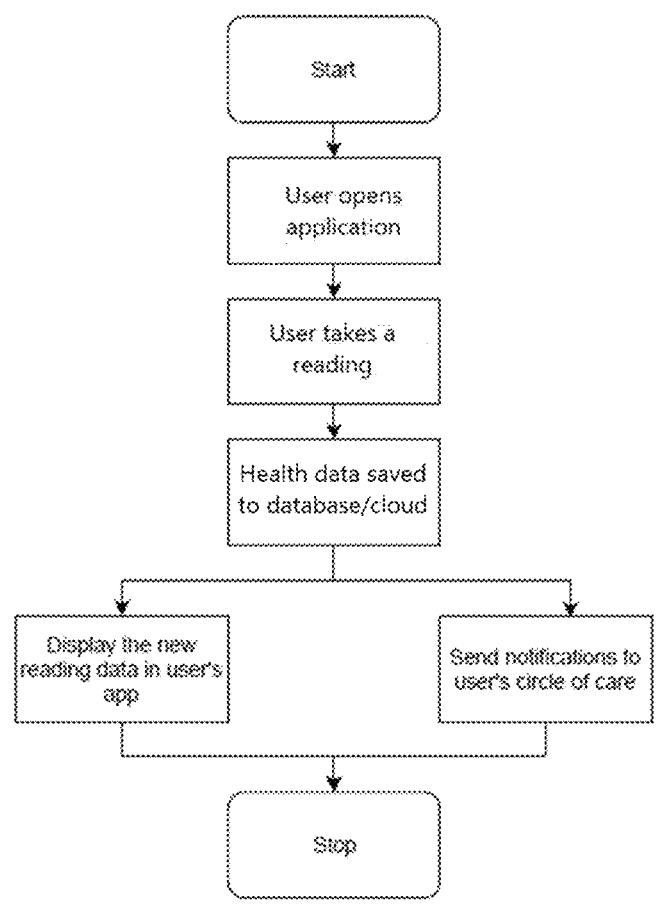
FIG. 14 illustrates a master workflow of an embodiment of a system for collecting, storing, manipulating and disseminating biometric telemetry data collected from a user.

FIG. 14 illustrates a master workflow for a user taking a reading of biometric data, and having the read data sent to selected POIs. To begin, a user opens the application on the SVS, and take a biometric reading using an appropriate device. The data is saved to the database on the cloud and displayed on user's SVS. In addition, notification of the reading is sent to the POIs.

Figure 15:
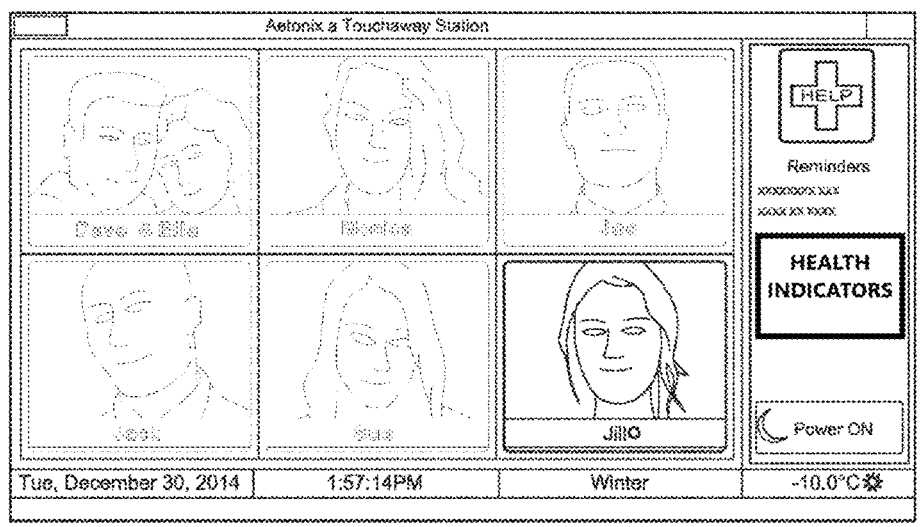
FIG. 15 illustrates an embodiment of a system for collecting, storing, manipulating and disseminating biometric telemetry data collected from a user, as displayed on an SVS screen.

FIG. 15 illustrates an example of an SVS screen with an icon "Health Indicators" which the user may touch to access information about previous health data and/or take a new reading of one more health indicators.

Figure 16:
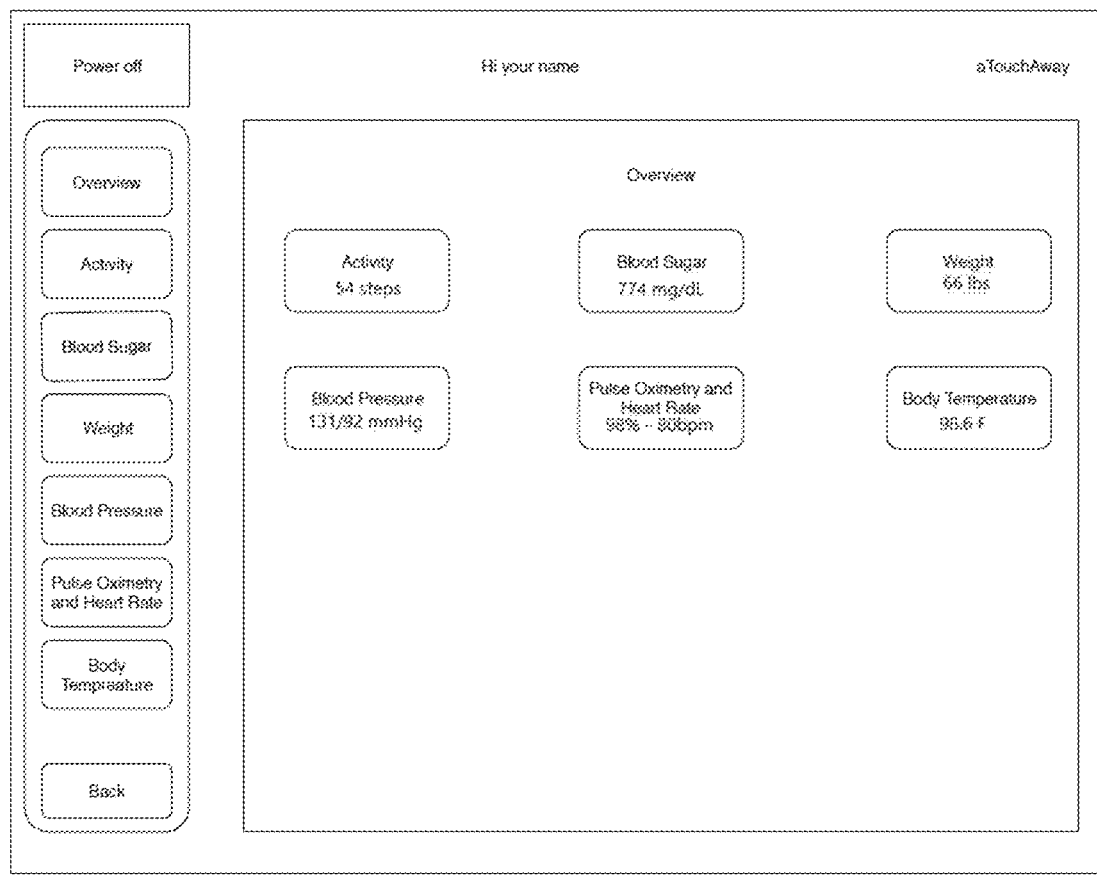
FIG. 16 illustrates further details of the embodiment shown in FIG. 15.

For example, when the user touches "Health Indicators", the SVS displays an overview of the most recent health data, as shown in FIG. 16. Included in the overview is a list of the most recent health data of the user. While six health indicators are shown, it is understood that more or fewer health indicators may be monitored. The screen also provides further access to specific health indicators (as shown in the column on the left), or, back to the main SVS screen (via the button "Back").

For example, if the user wishes to obtain further information on his/her pulse oximetry and heart rate, s/he can touch the "Pulse Oximetry and Heart Rate" button on the left. By doing so, the user is taken to a new screen, shown in FIG. 17, which provides more details about his/her pulse oximetry and heart rate. For example, the most current reading is provided, along with preceding measurements. This can also be represented in graphical format. The user has the option of entering a new reading manually or reading from a biometric device (to provide a new reading). A similar display is provided for the other health indictors.

Figure 17:
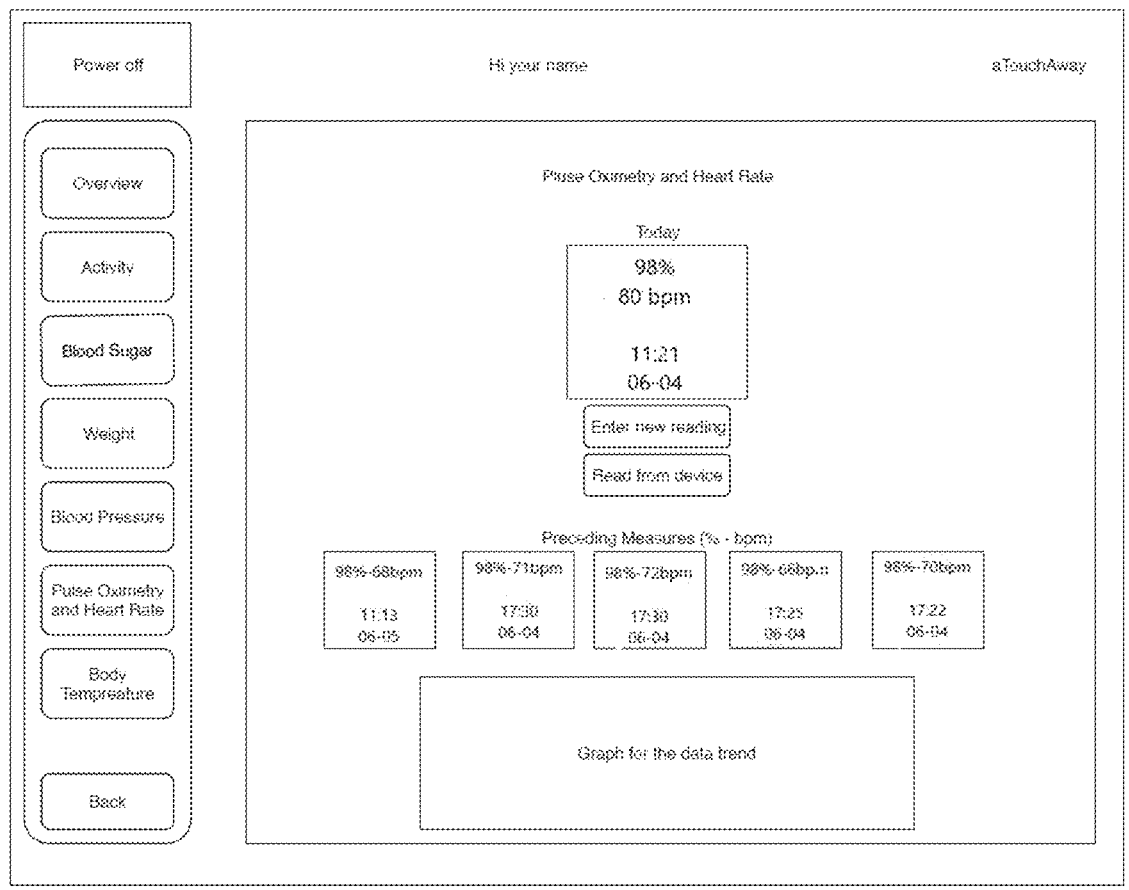
FIG. 17 illustrates further details of the embodiment shown in FIG. 16.
Figure 18:
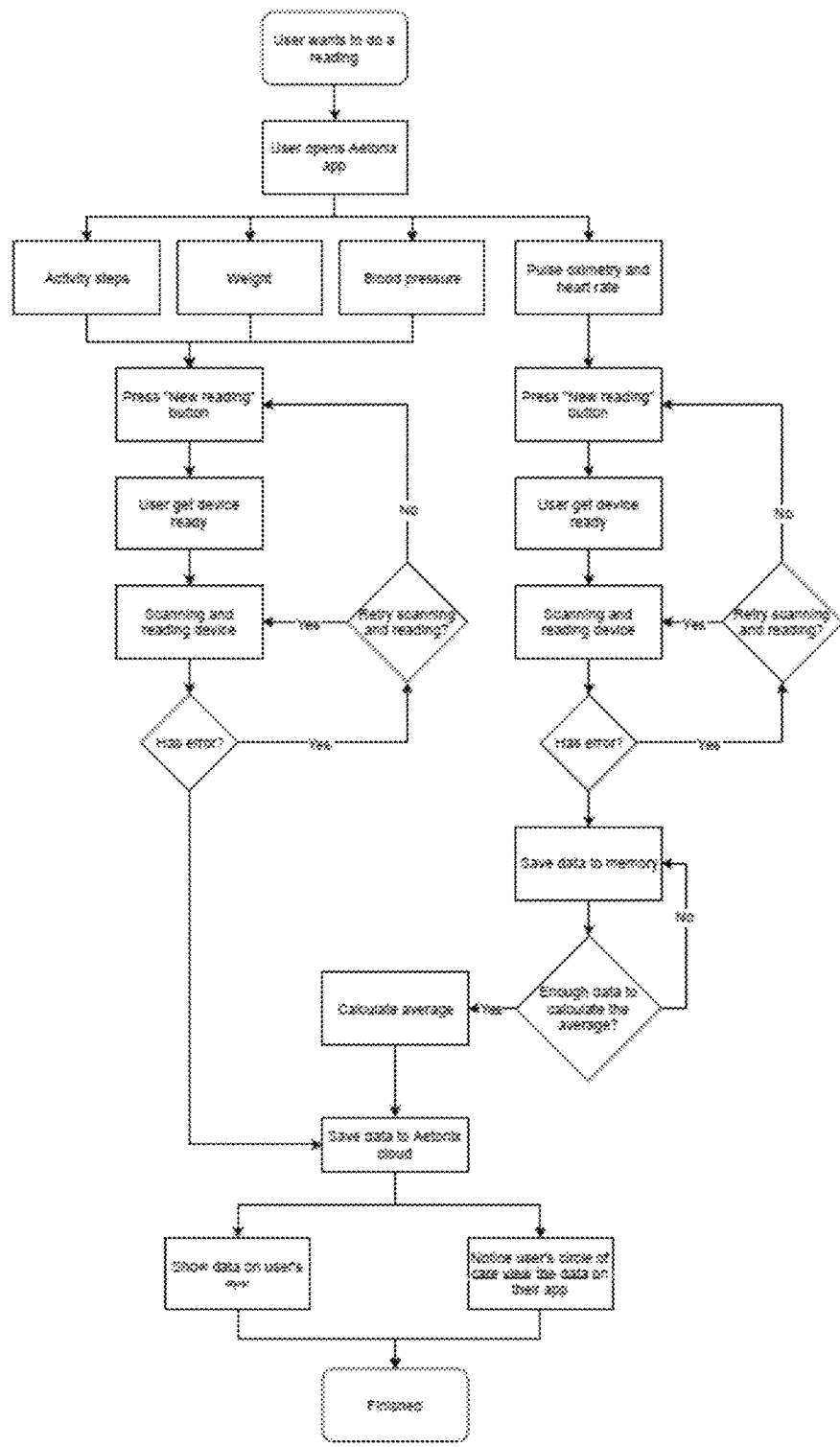
FIG. 18 illustrates a detailed workflow for steps regarding acquiring the biometric data in an embodiment of a system for collecting, storing, manipulating and disseminating biometric telemetry data collected from a user.

FIG. 18 illustrates a more detailed workflow for steps regarding acquiring the biometric data. A user opens the application on the SVS, and decides on a type of biometric data to read. For example, it may be activity steps, weight, blood pressure, pulse oximetry, heart rate, level of oxygen in the blood, etc. While four types of biometric data are shown in FIG. 18, it is understood that other types of health data can be read (as shown in FIGS. 16 and 17).

Once a type of biometric data is chosen, the user indicates to the SVS that a new reading is to be taken-either manually or through a device (as shown in FIG. 17). This can be accomplished by pressing either "enter new reading" or "read from device", as shown in FIG. 17.

If "enter new reading" is chosen, then the user is prompted to input the health data manually. On the other hand, if the user opts to use a device to take a health reading, a device module on the SVS receives information of the type of health reading that will be taken. The module will then load information particular to the type of biometric data that is to be acquired. The SVS may communicate with the biometric device using Bluetooth®, Zigbee® or other similar protocol.

For example, the device module can track the following information: the name of the device to search for; which Bluetooth Low-Energy (BLE) service and characteristic the module should write to in order to initialize the device in question; which BLE service characteristic it should read from in order to the particular health indicator information, and what text to display on the SVS at different steps during the measurement process.

The module will then prompt the user with a device-specific message to prompt the to prepare the device for taking readings. The biometric device can be any suitable device that allows for interfacing using Bluetooth®, Zigbee® or similar protocol known in the art.

The module will then begin scanning for nearby BLE devices and will see if the device's name matches the device needed to take the reading. If an appropriate device is not found within a certain pre-set time frame, the process will "time out" and prompt the user to take another reading. The pre-set time frame may be a few seconds to a few minutes.

If an appropriate device is found, the user will be notified that the reading is taking place and will see a graphical indicator regarding the stage of the measuring process. For example, a progress bar, or similar graphic, can be used, to mark the progress, or state of completion, of the reading.

Figure 19:
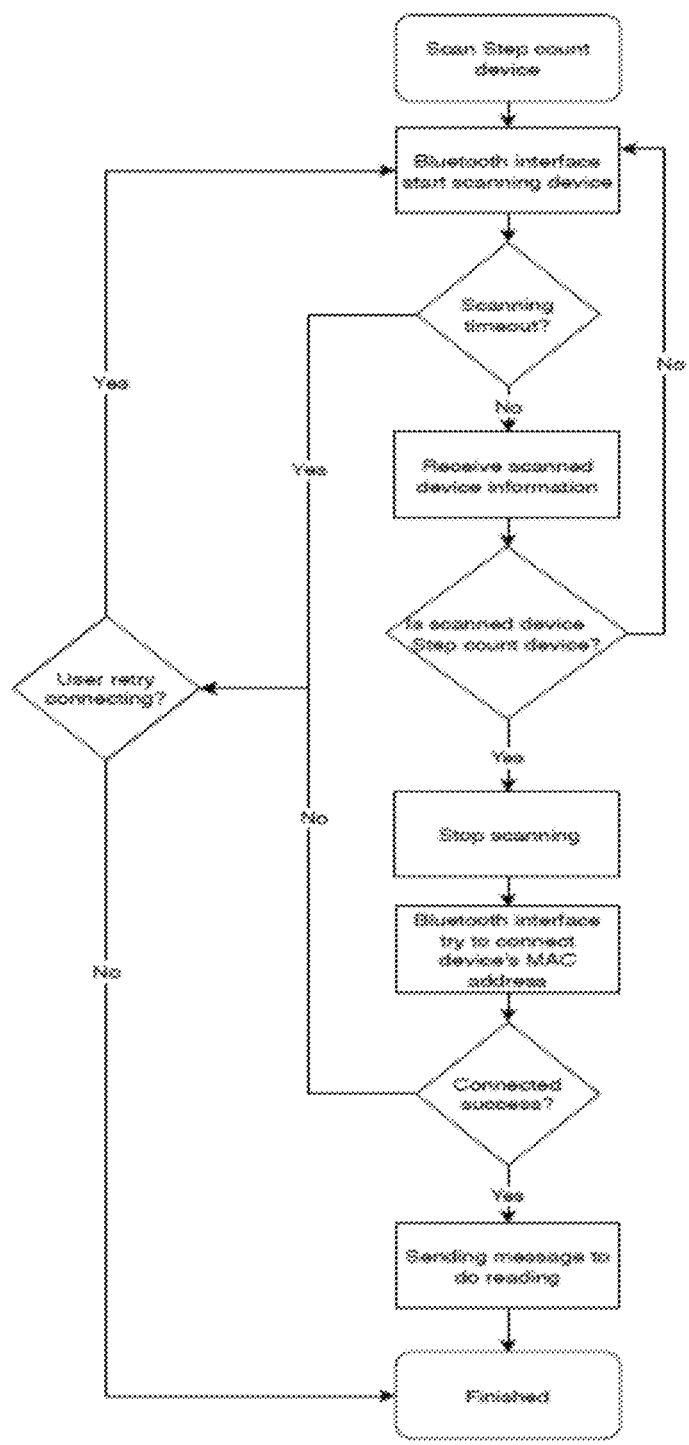
FIG. 19 illustrates a workflow for communication with a step count device in an embodiment of a system for collecting, storing, manipulating and disseminating biometric telemetry data collected from a user.

FIG. 19 illustrates a workflow for communication with a step count device. The user has indicated that s/he will take a step count reading from a biometric device. The SVS scans for devices using Bluetooth®. If no device is found within a certain timeframe, the user is prompted to either retry or end. If a device is found, its information is communicated to the SVS which checks to see if the found device is the step-count device. If it is not, then scanning continues, either until the step-count device is found, or the user decides to end the attempt to perform a reading.

Once the device is found, scanning is stopped. The Bluetooth® interface tries to connect with the step-count device's media access control (MAC) address. Once connected, a message is sent to the user (on the SVS) to do the reading until completed.

Some biometric data requires a single reading, while others require an average of readings.

As an example of a health indicator for which a simple reading is used, is a MetaWear® bracelet (from mbientlab) that tracks step counts. The module can listen on the BLE characteristic used for the step count readings. It can then write to a BLE characteristic to start the reading (if necessary). Once the reading event occurs, the module saves the health indicator to the database (in the cloud) and displays a "success" message to the user.

An example of a health indicator that requires the calculation of one or more averages, is the amount of oxygen in the blood. An exemplary device is a Nonin® pulse oximeter that measures an amount of oxygen in the blood. For such a reading, the module may start listening on the BLE characteristic for the reading. Once a new reading occurs, it's value is saved to memory (i.e. the application memory on the SVS). Once enough readings have been collected to perform a reliable average, an average of the reading is calculated. As with the single reading biometric data, once the average has been obtained, the module saves the health indicator to the database (in the cloud) and displays a "success" message to the user.

Figure 20:
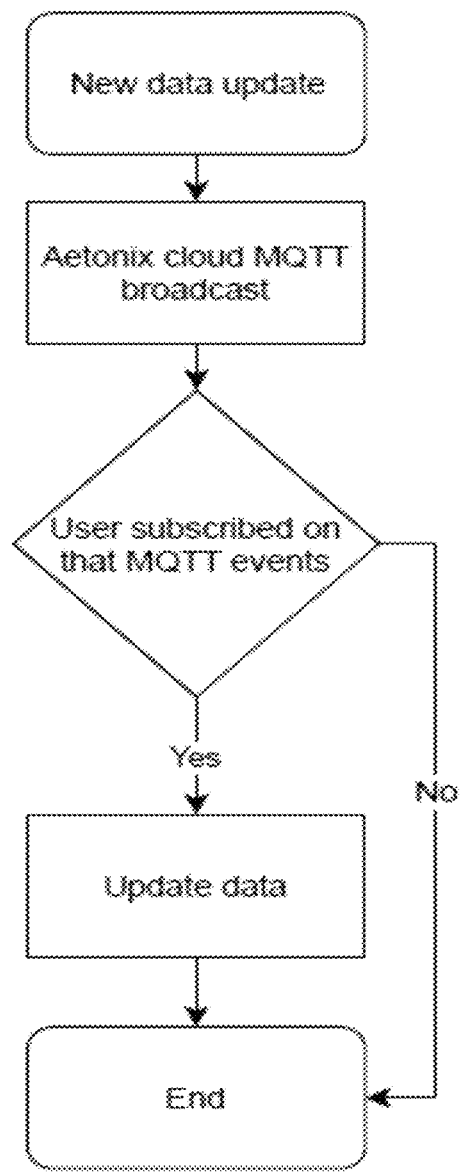
FIG. 20 illustrates a detailed workflow for sending an update of the biometric data to the POIs authorized to access the biometric data in an embodiment of a system for collecting, storing, manipulating and disseminating biometric telemetry data collected from a user.

FIG. 20 illustrates a more detailed workflow for sending an update of the biometric data to the POIs authorized to access the biometric data. Once the new readings have been sent to the database, an event will be generated for the MQTT broker, such that the cloud provides an MQTT broadcast. If a POI is authorized to receive the data (ie. subscribed to the particular MQTT event), then s/he will receive the biometric data. Thus, privacy is ensured such that only authorized POIs receive medical data.

Figure 21:
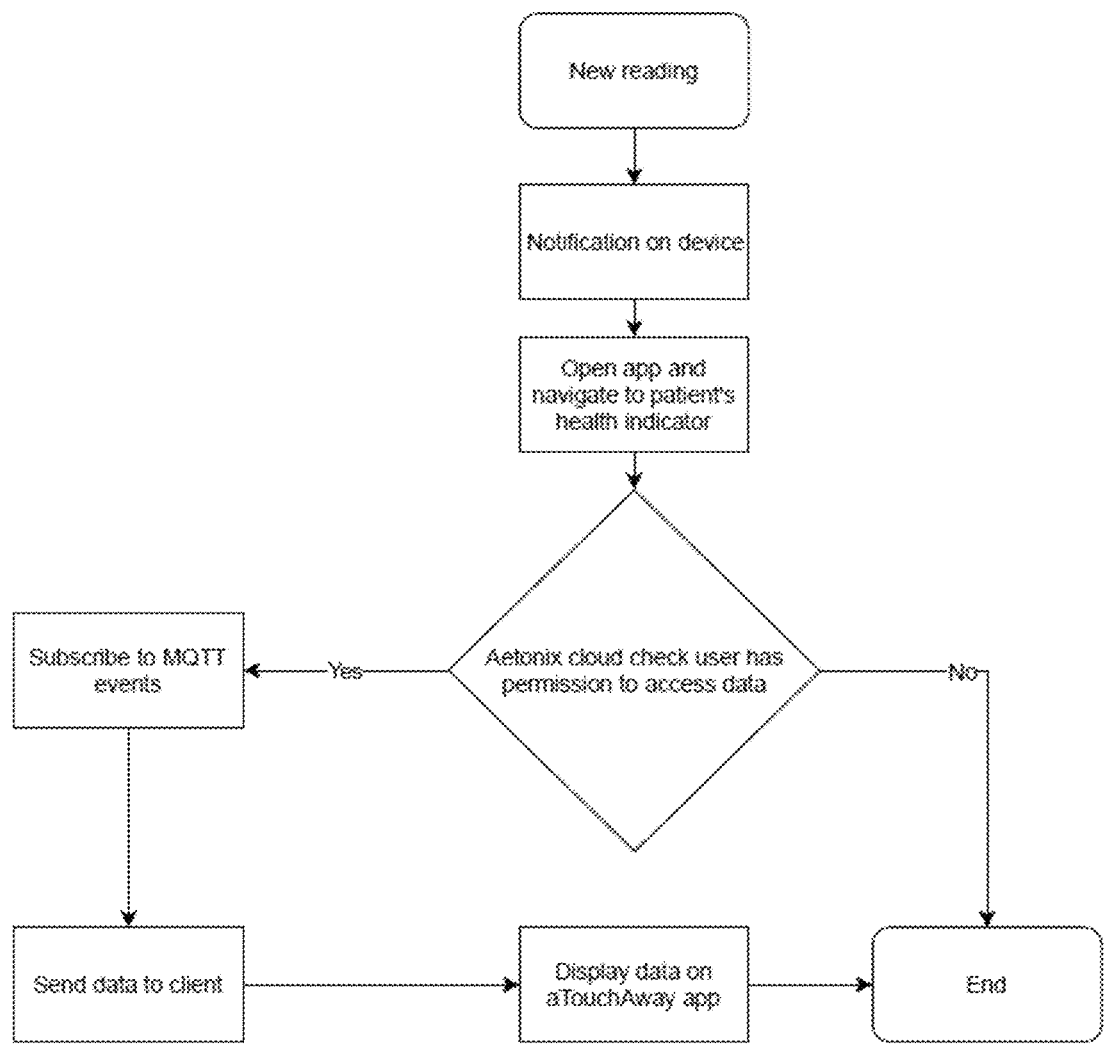
FIG. 21 illustrates a detailed workflow from the perspective of a POI in relation to the workflow of FIG. 20.

This is further detailed in FIG. 21, which illustrates a perspective from a POI. When a new reading is uploaded to the cloud, each POI does not get a push notification. Instead, his/her application receives an event with the updated data only if they are currently viewing the data (via MQTT). The POI may then open the application on the device to navigate to the user's health indicator data. The cloud then checks to make sure that the POI has permission to access the health indicator data. If not, then no further information is provided to the POI. If yes, then the POI subscribes to the MQTT event (for that particular health indicator data) and receives the specific health indicator data, which is then displayed on the POIs device via the application. Such a display may include trend of the data for a completed period of time (e.g. a few days, a week, two weeks, a month, etc.). In addition, the display may include a summary of the last few readings for that particular health indicator.

If the POI is in communication with the user, while the user is taking biometric data readings, and the POI is authorized to receive the data, then the MQTT event will enable the application on the POI's device to display the new data immediately (i.e. dynamically).

Workflow Engine for Healthcare Information Management

The workflow engine for healthcare information management disclosed herein differs from current such workflow engines by providing a dynamic platform: workflows can be updated for specific organizations in real-time without the need to update any applications. A workflow engine for healthcare information management disclosed herein is flexible enough to support any protocol involving collecting data from people, reacting to the collected data, and notifying others about data. The workflow engine uses high level components that make it easy to add features upon client demand.

The workflow engine has several practical uses. For example, it can be used to: help with medication regimens for post-surgery patients; do remote checkups on patients; and to automatically monitor patients' health.

The workflow engine is embedded into the platform (described above) and requires the software application described above to function. Workflows are all patient-centric in that the actors within a workflow include the patient, and all data collected is tied to the patient's records. Actors in a workflow are always a subset of a patient's circle of care (or POI).

An organization is entrusted to manage care of a patient. A workflow is required to manage this care. Members of the organization are POIs of the patient; this designation is also labeled as "the circle of care" for a patient. These members generate the workflows. To access the workflow engine, a POI must be given permission by an administrator when signed on. The POI then logs onto the workflow engine system, navigates to the patient, and accesses the workflow for that patient. S/he will receive a list of workflows for the patient. The workflow files are constructed and digitized by the workflow engine based on the organization's protocols. The POI will then choose from the list of workflows.

First, the system software application is used to communicate with the cloud server in order to fetch a list of workflow definitions from the database. The person interacting with the application will then select a workflow and use the forms engine to do initial configuration. When the form is "submitted", the data is sent to the cloud server which will send the data to the workflow runtime. The workflow runtime will load logic from the workflow definition in order to determine what the next steps are for the workflow. It will send commands back to the server which will then either send more actions to the applications used by actor within the workflow, or talk to the scheduler module to create tasks that will be processed at a later time, it will also send commands to the server to update information within the database. All the history of what happens in a workflow is stored in the database so that it can be reviewed by the patient's circle of care within the software application or exported externally for analysis.

Figure 22:
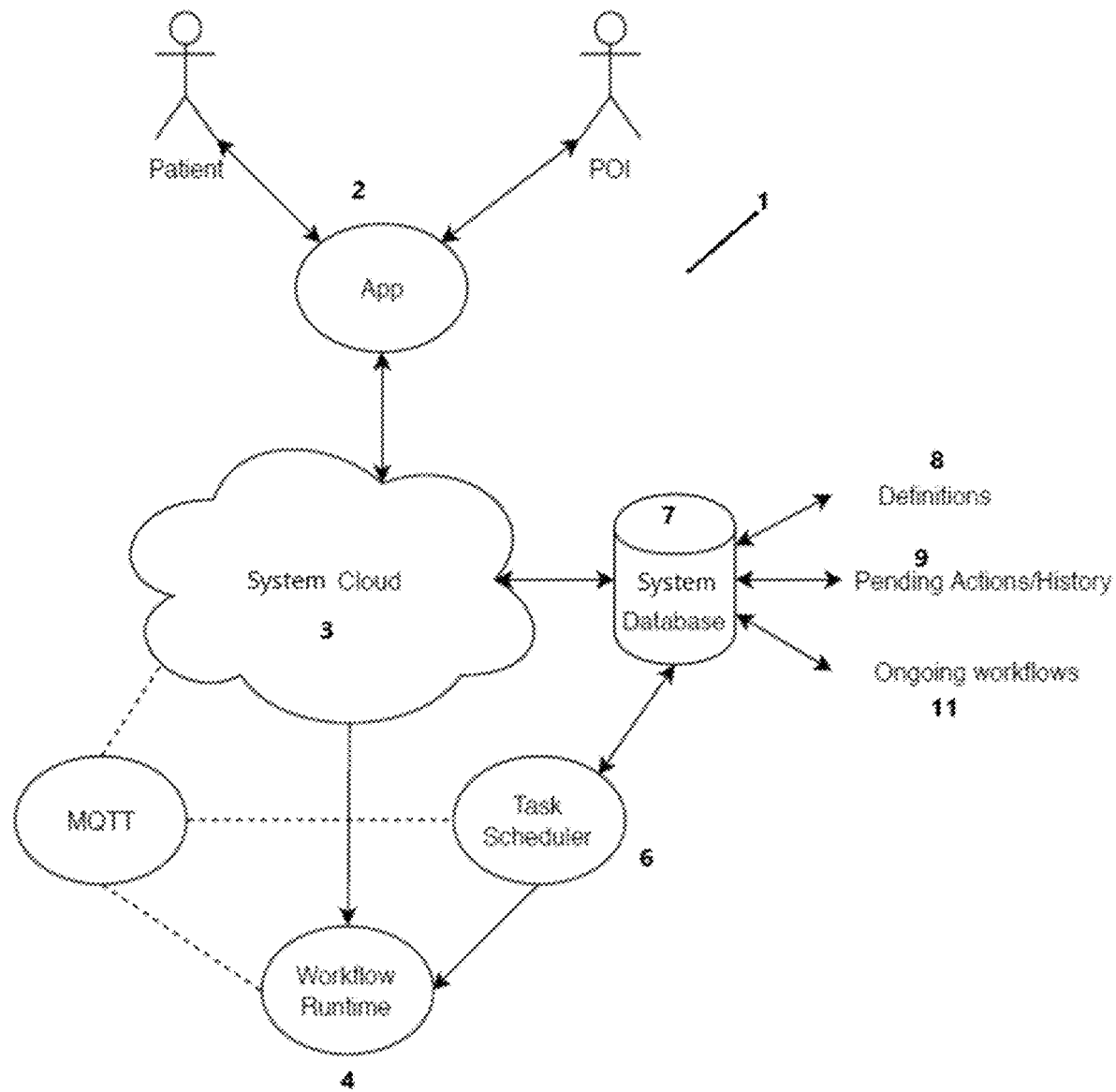
FIG. 22 illustrates a system architecture of an embodiment of a workflow engine for healthcare information management.

FIG. 22 illustrates a system architecture (1) of an embodiment of a workflow engine for healthcare information management.

The workflow engine comprises: a system application (2), a system cloud (3). a form engine in a system application (2); a workflow runtime component (4) in a system cloud (3), an action scheduler component (6) in the cloud (3); and a system database (7). The system database holds, for example, workflow definitions (8), pending actions/history (9) and ongoing workflows (11). In addition, the workflow engine also comprises a workflow definition file format. Each component is described below.

Forms Engine

The forms engine (in the system application) is used to dynamically generate user interfaces with real time validation logic for forms that are displayed to actors in the workflow. The forms engine can be used to capture and view any sort of data. This includes surveys, pictures, health indicators, medication prompts, etc.

The forms engine is also used to integrate with other features in system, such as taking readings of health indicators (either from biometric telemetry devices or from data input manually by the user), linking to the user's care plans, and making calls to actors in the workflow. The forms engine may support multiple languages within a single form definition in order to deploy the same workflow in multiple languages at once.

For example, the form engine can use a JavaScript Object Notification (JSON) schema for validation. It can also be used to describe fields in forms for "actions".

Each "property" in the schema has an "inputType" and a "displayType" for specifying how it should be displayed for inputting and for viewing. The form engine takes these schema definitions and generates a user interface with the appropriate inputs and outputs based on the schema contents. Schemas are in the JSON file format, so they can be easily loaded from the system cloud at runtime and allow for the addition and modification of forms in the application without needing to update the application itself. There are other formats that may be used to achieve the same result such as XML, HL7, YAML, Binary encoding, etc.

Workflow Runtime Component

The workflow runtime component is in the system cloud. In order to react to form submissions, a scripting language is used to decide what to do next after an actor in the workflow completes an action. This language is used in combination with certain Application Programming Interfaces (APIs) which are used for scheduling new actions and reactions, saving health information, and storing pieces of information used for the workflow logic.

The workflow runtime is integrated as part of the system cloud. It may use a JavaScript sandbox which isolates the scripting language from the rest of the operating system in order to ensure that scripts cannot do anything malicious. It can specify several JavaScript functions as being part of the "runtime" for scripts running as reactions. Furthermore, the runtime may contain a way to: inject the result of the form (as a JSON object); show actions to certain actors in the workflow; run other reactions to facilitate code-reuse; and to "schedule" actions or reactions to run at a later date using the CRON format or a Unix timestamp.

While JavaScript has been used in the example, it is understood that other scripting languages may also be used. Non-limiting examples include Lua; a meta-language using the same encoding as the rest of the workflow (e.g. XML); encoding commands using a custom format that doesn't use existing programming languages (e.g. creating a new language or "bytecode", using an encoding to describe commands).

An embodiment of the workflow engine includes integration of healthcare indicators with the Workflow Runtime and the system cloud. This allows workflows to save information about health indicators (for example, hearth rate, blood oxygen level, weight, body temperature, blood glucose, blood pressure, activity (step count), etc.). Forms using the Form Engine can take readings which will then be passed to workflow reactions in order to make decisions and to save for later use.

An Event broker can be used to relay events across the entire system. A broker based on a standard called MQTT which is used for "Internet Of Things" technologies may be used. Other event systems can be used.

Action Scheduler Component

The action scheduler component is in the system cloud. This component is used to schedule future events. For example, it can be used to schedule appointments, availability of actors, reminders, etc. The action scheduler can use the CRON standard to schedule tasks to run at a later time.

Workflow Definition File Format

The workflow definition file format describes workflows in a machine-readable way. This is uploaded to the system cloud for an organization in order to enable the organization to start workflows for their patients.

Use of a workflow definition in the workflow engine allows for the expression of any type of protocol that revolves around a patient and their care. The format allows for easy iteration of ideas, as well as allowing updates without requiring changes to the system infrastructure.

The workflow definition file format can be encoded in JSON to make it easy to parse in different environments and to generate workflow files. In this manner, it is geared to have everything that is needed for a workflow in a single file to make it easy to share. It also can contains fields for the forms that can be used with the form engine, the actor types, the reaction scripts, and configuration information.

While JSON encoding is used, it is understood that other types of encoding may be used in the workflow definition file format. Non-limiting examples include XML encoding, YAML encoding and custom "binary" encoding.

System Application and System Cloud

The system application and the system cloud form the system architecture that is used for delivering services and interfacing with all users of the system.

Figure 23:
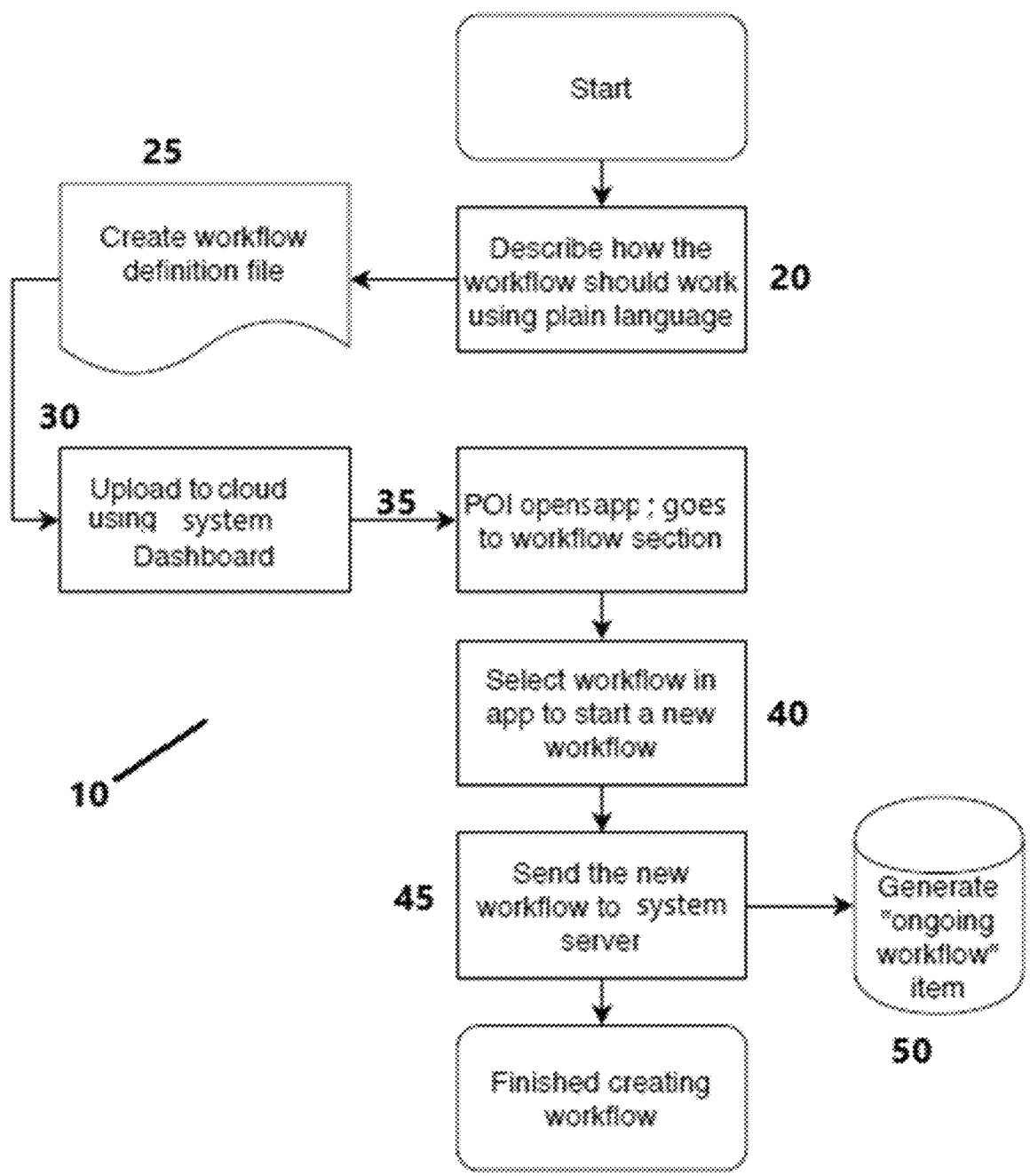
FIG. 23 illustrates a flowchart for creating/starting a workflow in an embodiment of a workflow engine for healthcare information management.

FIG. 23 illustrates a flowchart for creating/starting a workflow in an embodiment of a workflow engine for healthcare information management.

A description (20) of the workflow is used to create a workflow definition file (25), which can be uploaded (30) to the system cloud using a system dashboard. A POI subsequently opens (35) the software application to the patient's workflow information (contained in the workflow definition file). A new workflow is started by selecting (40) a workflow definition from a list of available workflows for that patient. At this stage, the workflow engine can optionally configure which "actor" labels in the workflow should point to which members of the patient's circle of care (i.e. POI). Furthermore, the workflow engine can optionally configure any initial parameters that the workflow requires to start (dynamically generated from the workflow definition). The workflow starts once the new workflow is sent (45) to the system database (50). This generates a new "ongoing workflow" item in the database in order to track the workflow state and associate it with the patient. If the workflow definition has an initial configuration, it will invoke the specified reaction with the configuration data in order to allow the workflow to decide how to start. An "Action" will be created which will record the identification of the actors from the workflow that should see this action, as well as which reaction should be invoked next.

Figure 24:
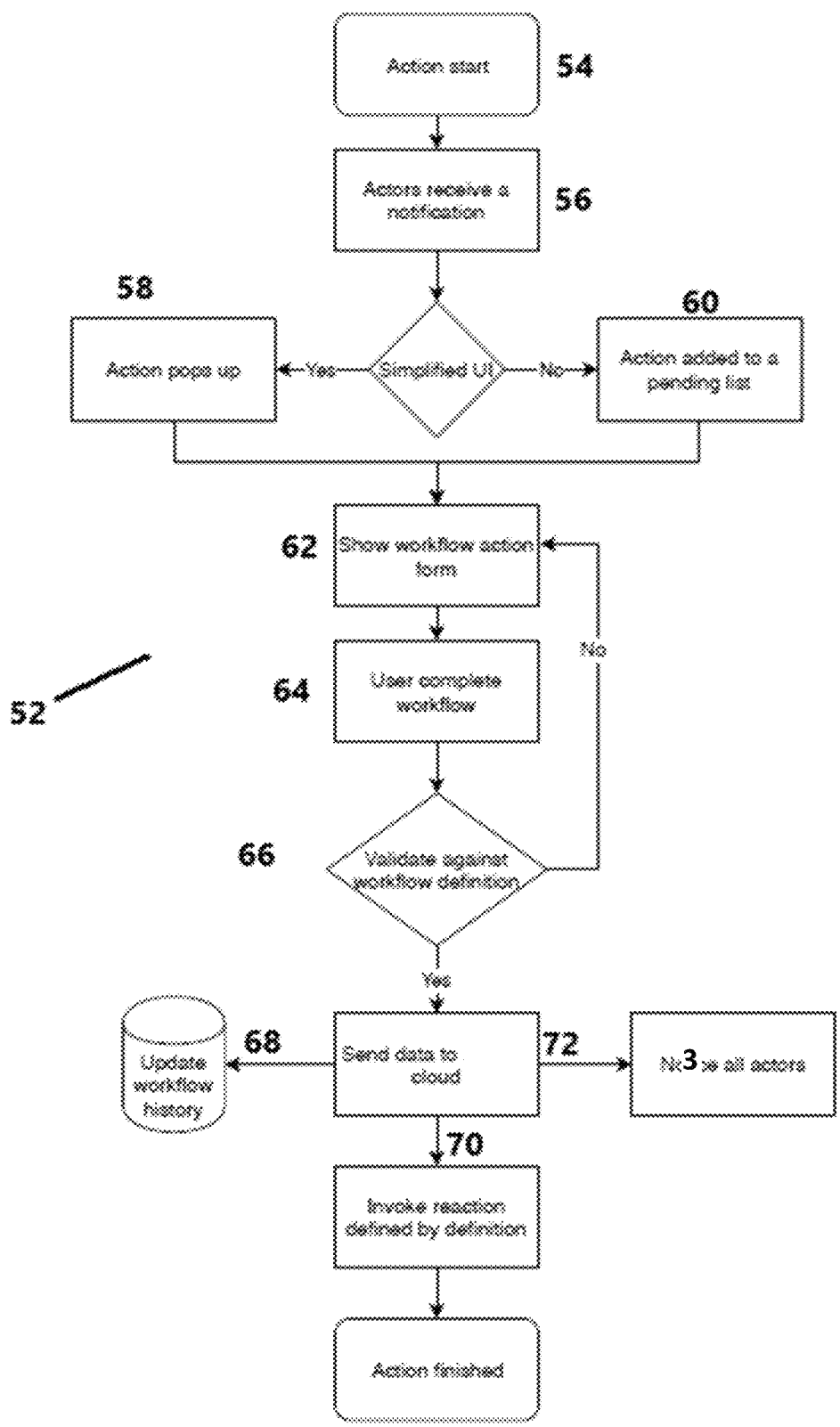
FIG. 24 illustrates a flowchart for starting an action in an embodiment of a workflow engine for healthcare information management.
Figure 25:
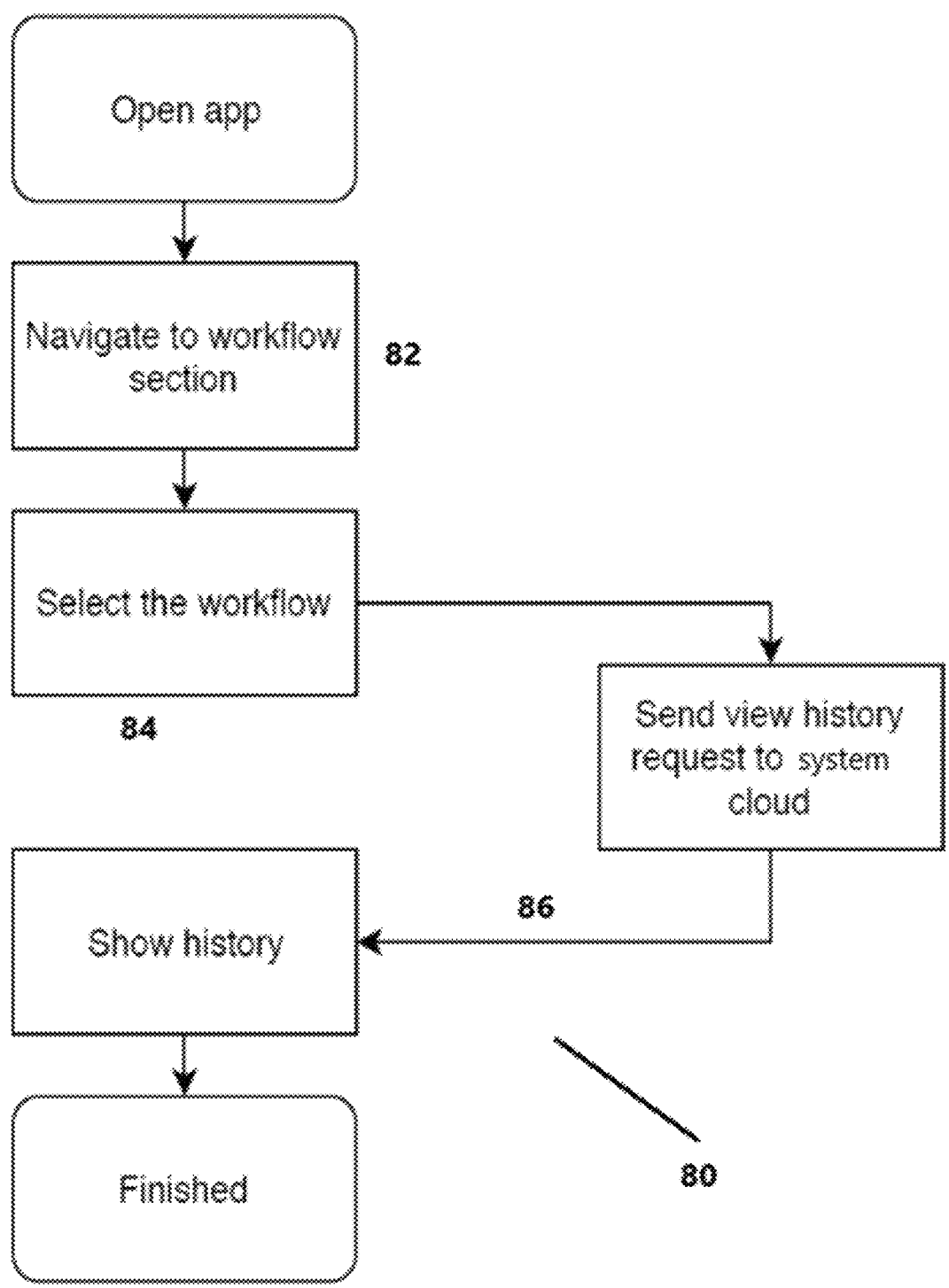
FIG. 25 illustrates a flowchart for viewing a history in an embodiment of a workflow engine for healthcare information management.

FIG. 24 illustrates a flowchart (52) for starting an action (54) in an embodiment of a workflow engine for healthcare information management.

All relevant actors in the list of POIs will receive (56) a combination of a push notification (if they have a mobile device) and an MQTT event (if they have the app open) which will notify them about the new action. Depending on the type of actor, the action will either pop up right away (58) (simplified UI for patients) or be added to a list at the top of the homepage and require the item to be accessed (60) (regular UI for POIs and patients who are familiar with technology).

The action will render (62) the relevant form based on the workflow definition using the Forms engine in the software application. Once the actor has filled (64) out the form, and submitted it, a request is sent to the cloud. The submitted data is validated (66) against the schema and will result in an error if something doesn't match. Otherwise it will continue by updating (68) the action's information and invoking a reaction (70). All actors receive (72) an MQTT event saying this action has been completed so that it can be removed from their list. Once the reaction script runs, the resulting commands are validated and then executed one at a time. These commands will result in either the state of the ongoing workflow to be updated; new actions to be sent or scheduled; other reaction scripts to run or be scheduled to run; health indicators to get saved; or other relevant actions.

A member of the patient's circle of care (i.e. a POI) can view the workflow history in the software application. The POI navigates (82) to the workflow section in the app; and select (84) the workflow for which they wish to view the history. The data is fetched (86) from the system cloud and MQTT events are set up to display any new actions or changes to actions. The schemas for the actions are used with the form engine in order to render the results.

Figure 26:
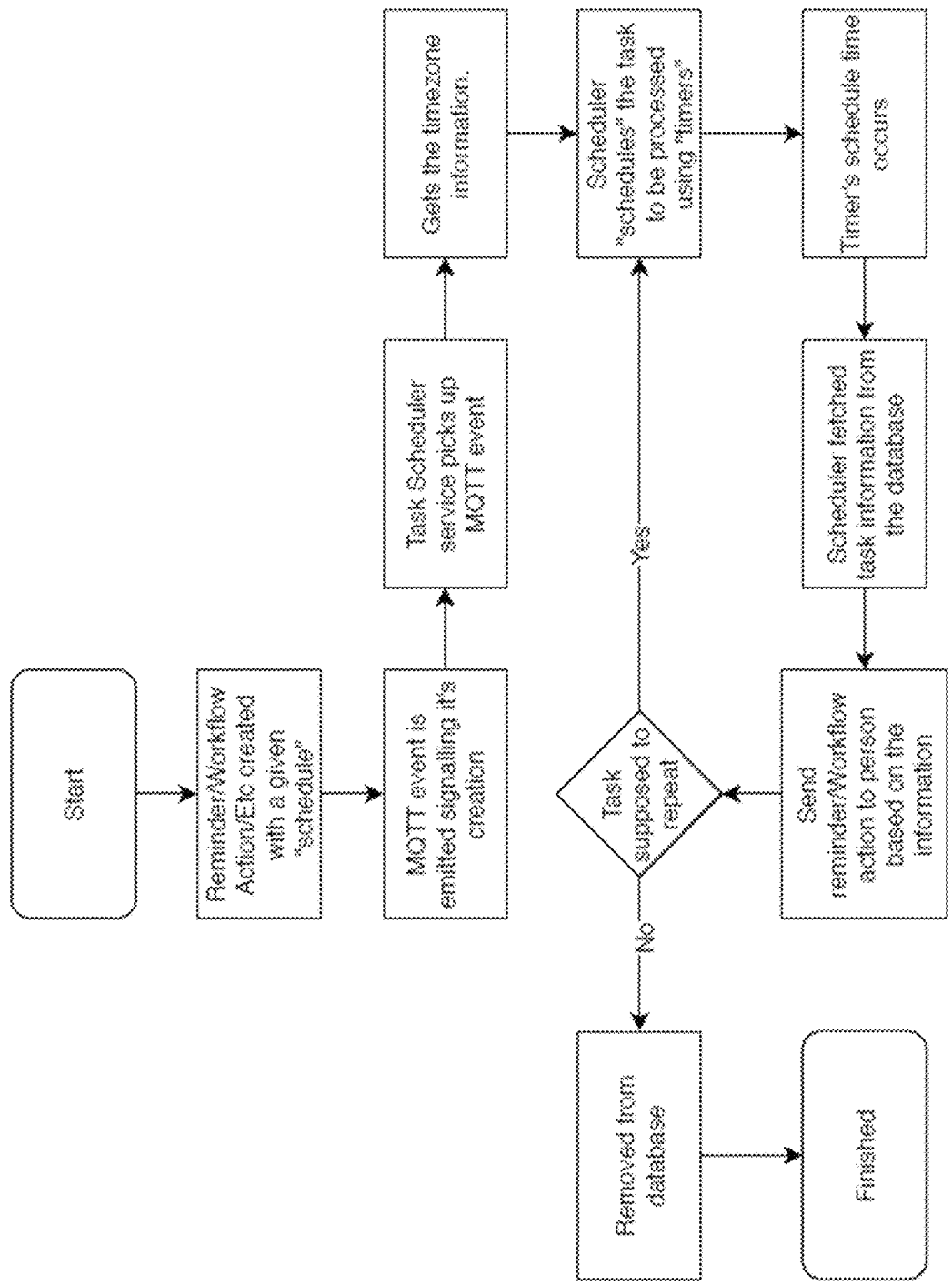
FIG. 26 illustrates a flowchart for scheduling a task in an embodiment of a workflow engine for healthcare information management.

FIG. 26 illustrates a flowchart for scheduling a task in an embodiment of a workflow engine for healthcare information management. The scheduler service starts up. It retrieves the list of all scheduled activities in the system. It parses the schedule for each task and determines the timestamp of when it should run. It sets up a timer per-task which will "run" the task at the appropriate time. It will also listen on MQTT events in order to add any newly scheduled tasks, and to cancel any tasks that are no longer needed. Depending on the type of task it will either send an action to the relevant actors in a workflow or run a reaction script. Once the task finishes running, it will be removed from the task list.

Example: Workflow for Medication Regimen

The workflow engine can manage a medication regiment for a patient. The steps are illustrated in FIGS. 27-31 and described below.

Figure 27:
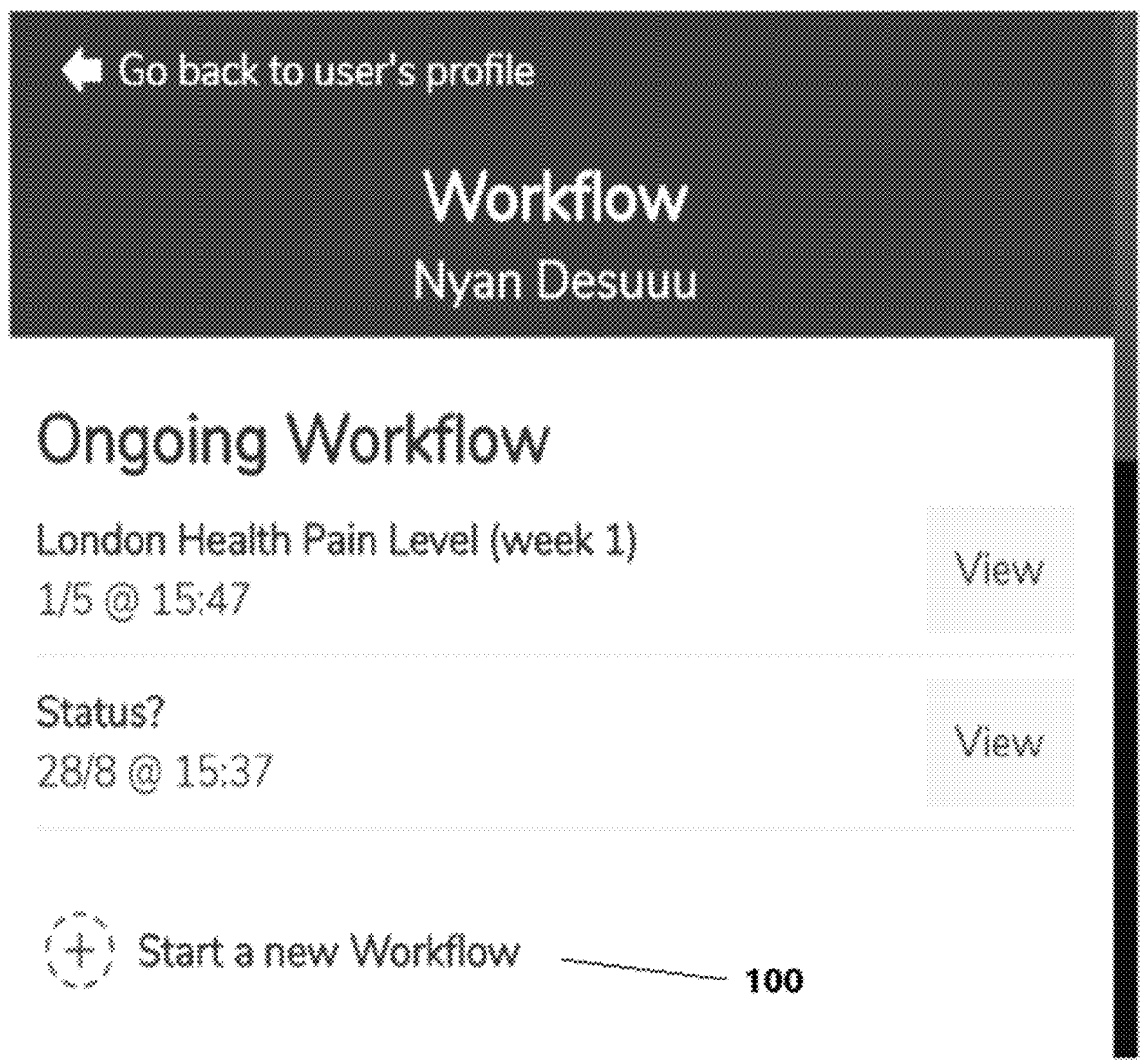
FIGS. 27-31 illustrate steps for managing a pain medication regimen for a patient in an embodiment of a workflow engine for healthcare information management.
Figure 28:
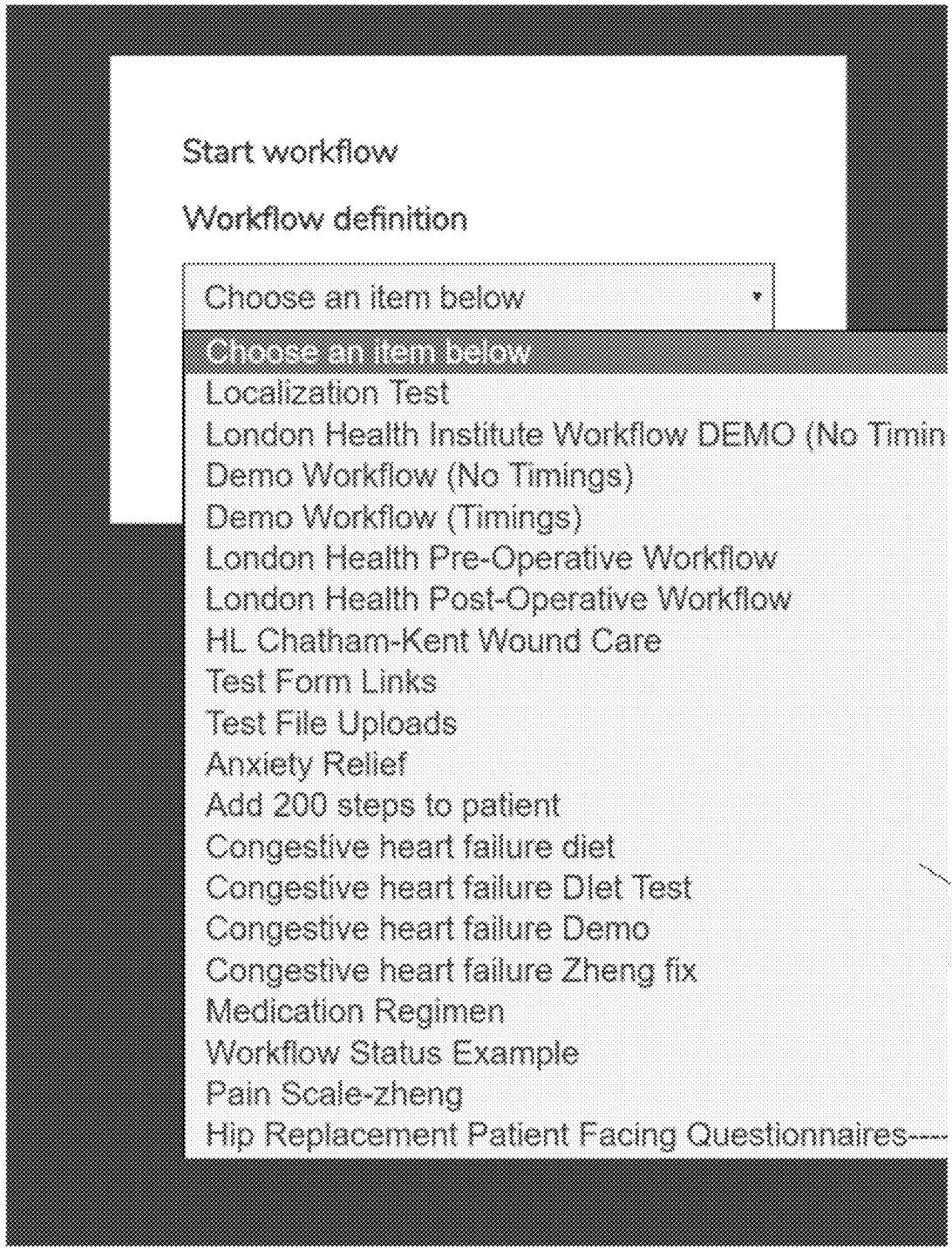
Figure 29:
Figure 30:
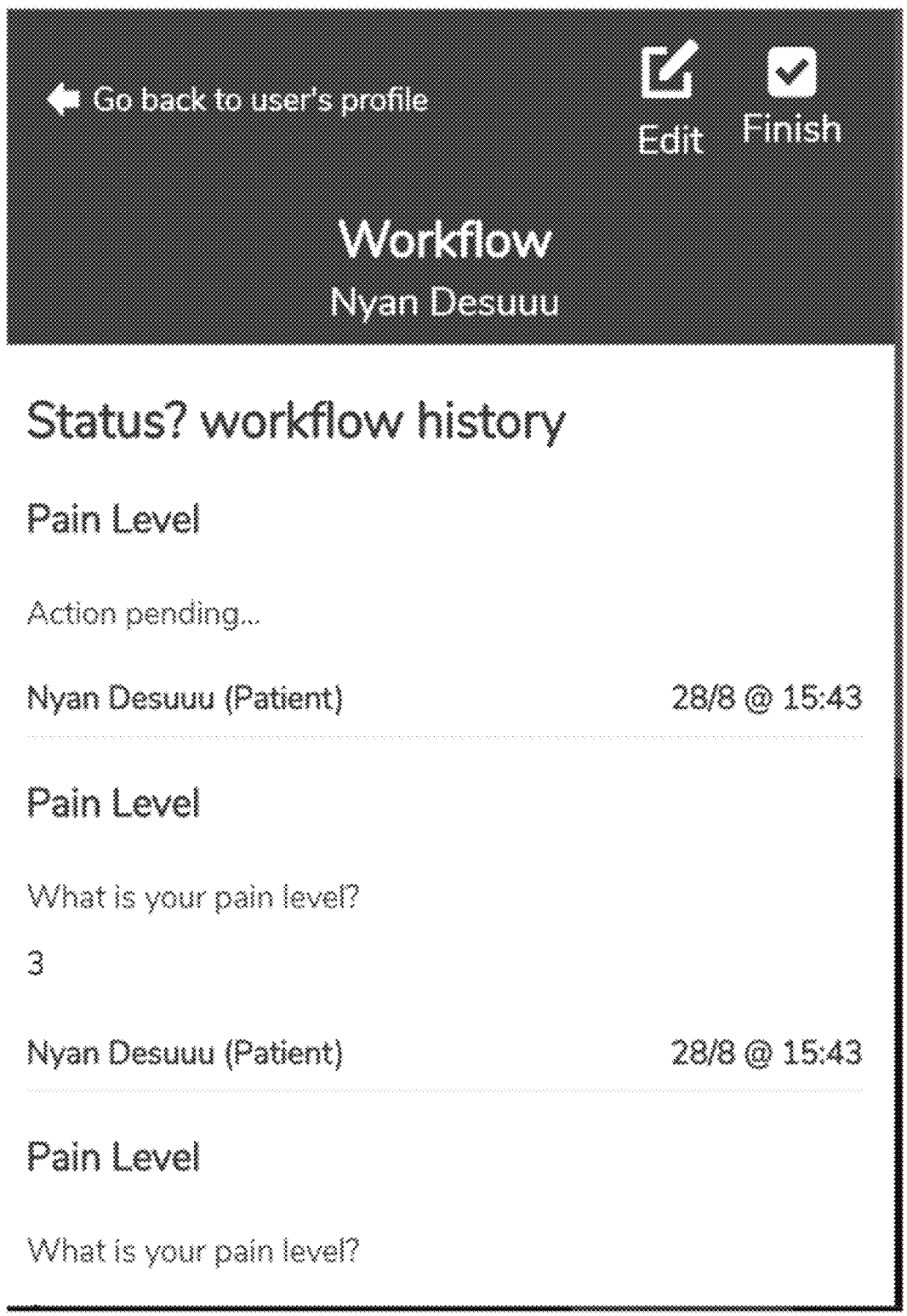
Figure 31:

In FIG. 27. a POI navigates to patient's "workflow" section and presses "start a new workflow" (100). In FIG. 28, the POI chooses the relevant workflow from a dropdown menu (105). In FIG. 29, the POI then fills out the form (110) with the medication names and times (there may be some default medications pre-filled). The POI finishes editing the form and presses "Save" on the form (not shown). This starts the workflow and will schedule the medications to be shown to the patient. The POI can visit the history of a workflow (pictured for a different workflow type) to see all the actions that have taken place (and the results), as shown in FIG. 30. The patient receives notification of workflow action (medication prompt) which they will acknowledge by pressing "DONE" as shown in FIG. 31.

Although the algorithms described above including those with reference to the foregoing flow charts have been described separately, it should be understood that any two or more of the algorithms disclosed herein can be combined in any combination. Any of the methods, algorithms, implementations, or procedures described herein can include machine-readable instructions for execution by: (a) a processor, (b) a controller, and/or (c) any other suitable processing device. Any algorithm, software, or method disclosed herein can be embodied in software stored on a non-transitory tangible medium such as, for example, a flash memory, a CD-ROM, a floppy disk, a hard drive, a digital versatile disk (DVD), or other memory devices, but persons of ordinary skill in the art will readily appreciate that the entire algorithm and/or parts thereof could alternatively be executed by a device other than a controller and/or embodied in firmware or dedicated hardware in a well known manner (e.g., it may be implemented by an application specific integrated circuit (ASIC), a programmable logic device (PLD), a field programmable logic device (FPLD), discrete logic, etc.). Also, some or all of the machine-readable instructions represented in any flowchart depicted herein can be implemented manually as opposed to automatically by a controller, processor, or similar computing device or machine. Further, although specific algorithms are described with reference to flowcharts depicted herein, persons of ordinary skill in the art will readily appreciate that many other methods of implementing the example machine readable instructions may alternatively be used. For example, the order of execution of the blocks may be changed, and/or some of the blocks described may be changed, eliminated, or combined.

It should be noted that the algorithms illustrated and discussed herein as having various modules which perform particular functions and interact with one another. It should be understood that these modules are merely segregated based on their function for the sake of description and represent computer hardware and/or executable software code which is stored on a computer-readable medium for execution on appropriate computing hardware. The various functions of the different modules and units can be combined or segregated as hardware and/or software stored on a non-transitory computer-readable medium as above as modules in any manner, and can be used separately or in combination.

While particular implementations and applications of the present disclosure have been illustrated and described, it is to be understood that the present disclosure is not limited to the precise construction and compositions disclosed herein and that various modifications, changes, and variations can be apparent from the foregoing descriptions without departing from the spirit and scope of an invention as defined in the appended claims.

The invention claimed is:

1. A system for managing healthcare of a patient by a pre-configured one or more actors, the one or more actors comprising one or more individuals having an affiliation to an organization, the system comprising:
   a processor; and
   a memory storing instructions, that when executed by the processor, configure the system to:
      create, by a first subset of the one or more actors, one or more workflow definitions from a workflow definition file, the workflow definition file being constructed and digitized based on a protocol of each organization;
      store the one or more workflow definitions in a database, wherein the database further includes privacy legislations and a signal library services for authentication of users and listening to events that happen with the delivery messages, upon determining that a message is delivered, events are raised to enable the signaling library to take action;
      select, by a second subset of the one or more actors, a workflow definition from the one or more workflow definitions;
      configurate, by the second subset, the selected workflow definition for the patient;
      generate a form related to the workflow definition, the form completed by an actor of the one more actors;
      receive data that is captured using the form, the data input by the actor;
      execute one or more subsequent steps using a workflow runtime, based on the data; and
      save the data into the database.

2. The system of claim 1, further configured to authenticate the one or more actors.

3. The system of claim 1, wherein the one or more subsequent steps comprises sending one or more action items to at least one actor of the one or more actors.

4. The system of claim 1, wherein the one or more subsequent steps comprises communicating with a task scheduler to create one or more tasks for processing at a later time.

5. The system of claim 4, wherein the task scheduler comprises at least one of: a medication regimen and monitoring health indicators of the patient.

6. The system of claim 1, wherein the data captured using the form is selected from the group consisting of surveys, images, one or more health indicators and medication prompts.

7. The system of claim 6, wherein the one or more health indicators include at least one of: information from one or more biometric telemetry devices and information input manually by the actor.

8. The system of claim 6, wherein the one or more health indicators is selected from the group consisting of heart rate, blood oxygen level, weight, body temperature, blood glucose, blood pressure and step count.

9. The system of claim 1, wherein the form is generated in a plurality of languages.

10. A computer-implemented method for managing healthcare of a patient by a pre-configured one or more actors, the one or more actors comprising one or more individuals having an affiliation to an organization, the method comprising:
- creating, by a first subset of the one or more actors, one or more workflow definitions from a workflow definition file, the workflow definition file being constructed and digitized based on a protocol of each organization;
- storing the one or more workflow definitions in a database, wherein the database further includes privacy legislations and a signal library services for authentication of users and listening to events that happen with the delivery messages, upon determining that a message is delivered, events are raised to enable the signaling library to take action;
- selecting, by a second subset of the one or more actors, a workflow definition from the one or more workflow definitions;
- configurating, by the second subset, the selected workflow definition for the patient;
- generating a form related to the workflow definition, the form completed by an actor of the one more actors;
- receiving data that is captured using the form, the data input by the actor;
- executing one or more subsequent steps using a workflow runtime based on the data; and
- saving the data into the database.

11. The method of claim 10, further comprising authentication of the one or more actors.

12. The method of claim 10, wherein the one or more subsequent steps comprises either:
- sending one or more action items to at least one actor of the one or more actors; or communicating with a task scheduler to create one or more tasks for processing at a later time.

13. The method of claim 12, wherein the task scheduler comprises at least one of: a medication regimen and monitoring one or more health indicators of the patient.

14. The method of claim 10, wherein the data captured by the form is selected from the group consisting of surveys, images, one or more health indicators and medication prompts.

15. The method of claim 14, wherein the one or more health indicators include at least one of: information from one or more biometric telemetry devices and information input manually by the actor.

16. The method of claim 14, wherein the one or more health indicators is selected from the group consisting of heart rate, blood oxygen level, weight, body temperature, blood glucose, blood pressure and step count.

17. A non-transitory computer-readable medium embodied with software, the software when executed using one or more computers is configured to:
- create, by a first subset of the one or more actors, one or more workflow definitions from a workflow definition file, the workflow definition file being constructed and digitized based on a protocol of each organization;
- store the one or more workflow definitions in a database, wherein the database further includes privacy legislations and a signal library services for authentication of users and listening to events that happen with the delivery messages, upon determining that a message is delivered, events are raised to enable the signaling library to take action;
- select, by a second subset of the one or more actors, a workflow definition from the one or more workflow definitions;
- generate a form related to the workflow definition, the form completed by an actor of the one more actors;
- configurate, by the second subset, the selected workflow definition for the patient;
- receive data that is captured using the form, the data input by the actor;
- execute one or more subsequent steps using a workflow runtime based on the data; and
- save the data into the database.

18. The non-transitory computer-readable medium of claim 17 further comprising authentication of the one or more actors.

19. The non-transitory computer-readable medium of claim 17 wherein the one or more subsequent steps comprises at least one of: sending one or more action items to at least one actor of the one or more actors and communicating with a task scheduler to create one or more tasks for processing at a later time.

20. The non-transitory computer-readable medium of claim 17, wherein the data captured by the form is selected from the group consisting of surveys, images, one or more health indicators and medication prompts; and the one or more health indicators is selected from the group consisting of heart rate, blood oxygen level, weight, body temperature, blood glucose, blood pressure and step count.

* * * * *